(12) United States Patent
Iwazawa et al.

(10) Patent No.: US 10,471,180 B2
(45) Date of Patent: Nov. 12, 2019

(54) CELL STRUCTURE AND METHOD FOR PRODUCING CELL STRUCTURE

(71) Applicant: FUJIFILM Corporation, Tokyo (JP)

(72) Inventors: Reiko Iwazawa, Ashigarakami-gun (JP); Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 198 days.

(21) Appl. No.: 15/374,604

(22) Filed: Dec. 9, 2016

(65) Prior Publication Data

US 2017/0100519 A1   Apr. 13, 2017

Related U.S. Application Data

(63) Continuation of application No. PCT/JP2015/066455, filed on Jun. 8, 2015.

(30) Foreign Application Priority Data

Jun. 10, 2014 (JP) .................. 2014-119372

(51) Int. Cl.

| | | |
|---|---|---|
| A61L 27/38 | (2006.01) | |
| A61L 27/22 | (2006.01) | |
| A61K 35/28 | (2015.01) | |
| A61L 27/00 | (2006.01) | |
| C07K 14/78 | (2006.01) | |
| A61L 27/50 | (2006.01) | |
| A61L 27/56 | (2006.01) | |

(52) U.S. Cl.
CPC .......... *A61L 27/3839* (2013.01); *A61K 35/28* (2013.01); *A61L 27/00* (2013.01); *A61L 27/222* (2013.01); *A61L 27/3808* (2013.01); *A61L 27/3834* (2013.01); *A61L 27/507* (2013.01); *A61L 27/56* (2013.01); *C07K 14/78* (2013.01); *A61L 2430/22* (2013.01); *A61L 2430/26* (2013.01)

(58) Field of Classification Search
None
See application file for complete search history.

(56) References Cited

U.S. PATENT DOCUMENTS

| 9,211,266 B2 | 12/2015 | Iwazawa et al. |
|---|---|---|
| 2012/0329157 A1 | 12/2012 | Nakamura et al. |
| 2013/0071441 A1 | 3/2013 | Iwazawa et al. |
| 2015/0202344 A1 | 7/2015 | Iwazawa et al. |
| 2015/0352252 A1 | 12/2015 | Nakamura et al. |
| 2016/0303282 A1 | 10/2016 | Nakamura et al. |

FOREIGN PATENT DOCUMENTS

| EP | 2 543 397 A1 | 1/2013 |
|---|---|---|
| EP | 2 543 398 A1 | 1/2013 |
| EP | 2 564 880 A1 | 3/2013 |
| EP | 2 698 173 A1 | 2/2014 |
| EP | 2 962 703 A1 | 1/2016 |
| EP | 3 050 580 A1 | 8/2016 |
| JP | 2011-512810 A | 4/2011 |
| JP | 2012-082245 A | 4/2012 |
| JP | 2014-012114 A | 1/2014 |
| WO | 2009/106641 A2 | 9/2009 |
| WO | 2011/108517 A1 | 9/2011 |
| WO | 2014/133081 A1 | 9/2014 |
| WO | 2015/046216 A1 | 4/2015 |

OTHER PUBLICATIONS

International Preliminary Report on Patentability issued from the International Bureau in counterpart International Application No. PCT/JP2015/066455, dated Dec. 22, 2016.
Communication dated Dec. 11, 2017, from the European Patent Office in counterpart European Application No. 15806620.9.
Extended European Search Report dated Mar. 21, 2017, from the European Patent Office in counterpart European Application No. 15806620.9.
Office Action dated Oct. 31, 2017, from the Japanese Patent Office in counterpart Japanese Application No. 2016-527792.
Tatsuya Shimizu et al., "Fabrication of Pulsatile Cardiac Tissue Grafts Using a Novel 3-Dimensional Cell Sheet Manipulation Technique and Temperature-Responsive Cell Culture Surfaces", Circ. Res., 2002, pp. 40-48, vol. 90.
Al Kushida et al., "Temperature-responsive culture dishes allow nonenzymatic harvest of differentiated Madin-Darby canine kidney (MDCK) cell sheets", J. Biomed. Mater. Res., 2000, pp. 216-223, vol. 51.
Al Kushida et al., "Decrease in culture temperature releases monolayer endothelial cell sheets together with deposited fibronectin matrix from temperature-responsive culture surfaces", J. Biomed. Mater. Res., 1999, pp. 355-362, vol. 45.
Tatsuya Shimizu et al., "Two-Dimensional Manipulation of Cardiac Myocyte Sheets Utilizing Temperature-Responsive Culture Dishes Augments the Pulsatile Amplitude", Tissue Engineering, Nov. 2, 2001, pp. 141-151, vol. 7, No. 2.

(Continued)

Primary Examiner — Michelle F. Paguio Frising
(74) Attorney, Agent, or Firm — Sughrue Mion, PLLC

(57) ABSTRACT

An object of the present invention is to provide a cell structure which does not contain glutaraldehyde and can form blood vessels after transplantation, and a method for producing the above-described cell structure. According to the present invention, there is provided a cell structure which contains a biocompatible macromolecular block and at least one kind of cell and has voids and in which a plurality of the biocompatible macromolecular blocks are arranged in gaps between a plurality of the cells, in which a ratio of the volume of the biocompatible macromolecular blocks with respect to the volume of the cell structure is 10% to 30%, a ratio of the volume of the cells with respect to the volume of the cell structure is 20% to 50%, and a ratio of the volume of the voids with respect to the volume of the cell structure is 35% to 60%.

17 Claims, 7 Drawing Sheets

Specification includes a Sequence Listing.

(56) References Cited

OTHER PUBLICATIONS

Tatsuya Shimizu et al., "Electrically communicating three-dimensional cardiac tissue mimic fabricated by layered cultured cardiomyocyte sheets", J. Biomed. Mater. Res., 2002, pp. 110-117, vol. 60.

Masami Harimoto et al., "Novel approach for achieving double-layered cell sheets co-culture: overlaying endothelial cell sheets onto monolayer hepatocytes utilizing temperature-responsive culture dishes", J. Biomed. Mater. Res., 2002, pp. 464-470, vol. 62.

Tatsuya Shimizu et al., "Cell sheet engineering for myocardial tissue reconstruction", Biomaterials, 2003, pp. 2309-2316, vol. 24.

Teruo Okano, "Fusion of Inflammation and Regeneration Researches", The 26th Annual Meeting of the Japanese Society of Inflammation and Regeneration, Inflammation and Regeneration, 2005, pp. 158-159, vol. 25, No. 3.

International Search Report of PCT/JP2015/066455 dated Aug. 18, 2015 [PCT/ISA/210].

Written Opinion of PCT/JP2015/066455 dated Aug. 18, 2015 [PCT/ISA/237].

SEQUENCE LISTING

```
<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic peptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95
```

-continued

```
Gly Glu Arg Gly Ala Ala Gly Leu Pro Gly Pro Lys Gly Glu Arg Gly
                100                 105                 110
Asp Ala Gly Pro Lys Gly Ala Asp Gly Ala Pro Gly Lys Asp Gly Val
            115                 120                 125
Arg Gly Leu Ala Gly Pro Ile Gly Pro Pro Gly Pro Ala Gly Ala Pro
        130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                165                 170                 175
Asp Gly Ala Pro Gly Lys Asp Gly Val Arg Gly Leu Ala Gly Pro Pro
            180                 185                 190
Gly Ala Pro Gly Leu Gln Gly Ala Pro Gly Leu Gln Gly Met Pro Gly
        195                 200                 205
Glu Arg Gly Ala Ala Gly Leu Pro Gly Pro Lys Gly Glu Arg Gly Asp
    210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Ala Gly Pro Lys Gly Ala Asp Gly Ala Pro Gly Lys
            260                 265                 270
Asp Gly Val Arg Gly Leu Ala Gly Pro Ile Gly Pro Pro Gly Glu Arg
        275                 280                 285
Gly Ala Ala Gly Leu Pro Gly Pro Lys Gly Glu Arg Gly Asp Ala Gly
    290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
            340                 345                 350
Pro Lys Gly Glu Arg Gly Asp Ala Gly Pro Lys Gly Ala Asp Gly Ala
        355                 360                 365
Pro Gly Lys Asp Gly Val Arg Gly Leu Ala Gly Pro Pro Gly Ala Pro
    370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
        435                 440                 445
Asp Ala Gly Pro Lys Gly Ala Asp Gly Ala Pro Gly Lys Asp Gly Val
    450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
```

```
                515                 520                 525
Gly Met Pro Gly Glu Arg Gly Ala Ala Gly Leu Pro Gly Pro Lys Gly
    530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Leu Gly Thr Ile Pro Gly
1               5

<210> SEQ ID NO 7
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(571)
<223> OTHER INFORMATION: all Xaa is independently any amino acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
```

```
                85                  90                  95
Gly Xaa Xaa Gly Xaa Xaa Gly Xaa Xaa Gly Xaa Xaa Gly
            100                 105                 110
Xaa Xaa Gly Xaa Xaa Gly Xaa Xaa Gly Xaa Xaa Gly Xaa
            115                 120                 125
Xaa Gly Xaa Xaa Gly Xaa Xaa Gly Xaa Xaa Gly Xaa Xaa
            130                 135                 140
Gly Xaa Xaa Gly Xaa Xaa Gly Xaa Xaa Gly Xaa Xaa Gly
145                 150                 155                 160
Xaa Xaa Gly Xaa Xaa Gly Xaa Xaa Gly Xaa Xaa Gly Xaa
                165                 170                 175
Xaa Gly Xaa Xaa Gly Xaa Xaa Gly Xaa Xaa Gly Xaa Xaa
            180                 185                 190
Gly Xaa Xaa Gly Xaa Xaa Gly Xaa Xaa Gly Xaa Xaa Gly
            195                 200                 205
Xaa Xaa Gly Xaa Xaa Gly Xaa Xaa Gly Xaa Xaa Gly Xaa
            210                 215                 220
Xaa Gly Xaa Xaa Gly Xaa Xaa Gly Xaa Xaa Gly Xaa Xaa
225                 230                 235                 240
Gly Xaa Xaa Gly Xaa Xaa Gly Xaa Xaa Gly Xaa Xaa Gly
                245                 250                 255
Xaa Xaa Gly Xaa Xaa Gly Xaa Xaa Gly Xaa Xaa Gly Xaa
            260                 265                 270
Xaa Gly Xaa Xaa Gly Xaa Xaa Gly Xaa Xaa Gly Xaa Xaa
            275                 280                 285
Gly Xaa Xaa Gly Xaa Xaa Gly Xaa Xaa Gly Xaa Xaa Gly
            290                 295                 300
Xaa Xaa Gly Xaa Xaa Gly Xaa Xaa Gly Xaa Xaa Gly Xaa
305                 310                 315                 320
Xaa Gly Xaa Xaa Gly Xaa Xaa Gly Xaa Xaa Gly Xaa Xaa
                325                 330                 335
Gly Xaa Xaa Gly Xaa Xaa Gly Xaa Xaa Gly Xaa Xaa Gly
            340                 345                 350
Xaa Xaa Gly Xaa Xaa Gly Xaa Xaa Gly Xaa Xaa Gly Xaa
            355                 360                 365
Xaa Gly Xaa Xaa Gly Xaa Xaa Gly Xaa Xaa Gly Xaa Xaa
            370                 375                 380
Gly Xaa Xaa Gly Xaa Xaa Gly Xaa Xaa Gly Xaa Xaa Gly
385                 390                 395                 400
Xaa Xaa Gly Xaa Xaa Gly Xaa Xaa Gly Xaa Xaa Gly Xaa
                405                 410                 415
Xaa Gly Xaa Xaa Gly Xaa Xaa Gly Xaa Xaa Gly Xaa Xaa
            420                 425                 430
Gly Xaa Xaa Gly Xaa Xaa Gly Xaa Xaa Gly Xaa Xaa Gly
            435                 440                 445
Xaa Xaa Gly Xaa Xaa Gly Xaa Xaa Gly Xaa Xaa Gly Xaa
            450                 455                 460
Xaa Gly Xaa Xaa Gly Xaa Xaa Gly Xaa Xaa Gly Xaa Xaa
465                 470                 475                 480
Gly Xaa Xaa Gly Xaa Xaa Gly Xaa Xaa Gly Xaa Xaa Gly
                485                 490                 495
Xaa Xaa Gly Xaa Xaa Gly Xaa Xaa Gly Xaa Xaa Gly Xaa
            500                 505                 510
```

-continued

```
Xaa Gly Xaa Xaa Gly Xaa Xaa Gly Xaa Xaa Gly Xaa Xaa
        515                 520             525

Gly Xaa Xaa Gly Xaa Xaa Gly Xaa Xaa Gly Xaa Xaa Gly
    530             535             540

Xaa Xaa Gly Xaa Xaa Gly Xaa Xaa Gly Xaa Xaa Gly Xaa
545         550             555             560

Xaa Gly Xaa Xaa Gly Xaa Xaa Gly Xaa Xaa Gly
            565             570
```

CELL STRUCTURE AND METHOD FOR PRODUCING CELL STRUCTURE

CROSS-REFERENCE TO RELATED APPLICATIONS

The present application is a continuation of PCT/JP2015/066455 filed on Jun. 8, 2015 and claims priority under 35 U.S.C. § 119 of Japanese Patent Application No. 119372/2014 filed on Jun. 10, 2014.

BACKGROUND OF THE INVENTION

1. Field of the Invention

The present invention relates to a cell structure and a method for producing a cell structure. Specifically, the present invention relates to a cell structure which can form a blood vessel after transplantation, and a production method thereof.

2. Description of the Related Art

Currently, regenerative medicine, which regenerates living body tissues and organs having functional disorders or dysfunction, is put into practical use. The regenerative medicine is new medical technology creating a form or a function of a living body tissue that cannot be recovered with only natural healing ability possessed by a living body, which is the same as that of an original tissue, again, using three factors including a cell, a scaffold, and a growth factor. In recent years, treatment using cells is gradually realized. Examples thereof include cartilage treatment using autologous chondrocytes, and cultured epidermis using autologous cells; bone regeneration treatment using mesenchymal stem cells; myocardial cell sheet treatment using myoblasts; cornea regeneration treatment using corneal epithelial sheets; and nerve regeneration treatment. These kinds of new treatment are different from alternative medicine (for example, a bone prosthetic material or hyaluronic acid injection) using an artifact in the related art, and repair and regenerate biological tissues, thereby obtaining a high treatment effect. Actually, products such as cultured epidermis or cultured cartilage using autologous cells have been available on the market.

For example, when regenerating the myocardium using cell sheets, it is considered that a multilayer structure of the cell sheets is required in order to regenerate a tissue with thickness. In recent years, Okano et al. have developed a cell sheet using a temperature-responsive culture dish. Since the cell sheet does not require enzymatic treatment using trypsin or the like, bonding between cells and adhesive proteins are maintained (Shimizu, T. et al., Circ. Res. 90, e40-48 (2002), Kushida, A. et al., J. Biomed. Mater. Res. 51, 216-223 (2000), Kushida, A. et al., J. Biomed. Mater. Res. 45, 355-362 (1999), Shimizu, T., Yamato, M., Kikuchi, A. & Okano, T., Tissue Eng. 7, 141-151 (2001), Shimizu, T et al., J. Biomed. Mater. Res. 60, 110-117(2002), and Harimoto, M. et al., J. Biomed. Mater. Res. 62, 464-470 (2002)). It is anticipated that a technology for producing such a cell sheet will be useful for regeneration of myocardial tissues (Shimizu, T., Yamato, M., Kikuchi, A. & Okano, T., Biomaterials 24, 2309-2316 (2003)). In addition, Okano et al. have developed a cell sheet in which it is necessary to form a vascular plexus and to which vascular endothelial cells are introduced together (Inflammation and Regeneration vol. 25 No. 3 2005, p 158-159. The 26th Annual Meeting of the Japanese Society of Inflammation and Regeneration, "Fusion of Inflammation and Regeneration Researches", Teruo OKANO).

In addition, a cell structure, which contains cells and macromolecular blocks having biocompatibility, and in which the plurality of the above-described macromolecular blocks are arranged in gaps between the plurality of the above-described cells, is disclosed in WO2011/108517A. In the cell structure disclosed in WO2011/108517A, it is possible to deliver nutrients to the inside of the cell structure from the outside. The cell structure has a sufficient thickness, and cells exist in the structure uniformly. In Example of WO2011/108517A, high cell survival activity is verified using a macromolecular block formed of a recombinant gelatin material or a natural gelatin material. A cell structure for cell transplantation, which contains a macromolecular block having biocompatibility and at least one kind of cell, and in which the plurality of the above-described macromolecular blocks are arranged in the gaps between the plurality of the above-described cells, is disclosed in JP2014-12114A. In Example of JP2014-12114A, angiogenesis is evaluated using the cell structure for cell transplantation.

SUMMARY OF THE INVENTION

In the macromolecular block of the cell structure disclosed in Examples of WO2011/108517A and JP2014-12114A, glutaraldehyde is used for cross-linking of macromolecules. In order for cell transplantation treatment performed on a human body, it is desirable to use a cell structure which is produced through a method in which glutaraldehyde is not used. However, the cell structure which is produced through the method, in which glutaraldehyde is not used, and in which it is possible to form blood vessels after transplantation, has not yet been provided.

An object of the present invention is to provide a cell structure which does not contain glutaraldehyde and can form blood vessels after transplantation. Furthermore, another object of the present invention is to provide a method for producing the above-described cell structure.

The present inventors have conducted intensive studies in order to solve the above-described problems. As a result, they have succeeded in forming blood vessels in a cell structure which has the biocompatible macromolecular blocks, the cells, and voids, by setting proportions of the volume of biocompatible macromolecular blocks, the volume of cells, and the volume of voids with respect to the volume of the cell structure to 10% to 30%, 20% to 50%, and 35% to 60%, in the cell structure. Furthermore, the present inventors have also succeeded in maintaining blood vessels over a long period of time in a cell structure containing vascular endothelial precursor cells in a case where the cell structure is transplanted under the renal capsule, and have completed the present invention based on these findings.

That is, according to the present invention, there are provided inventions as follows.

(1) A cell structure which contains a biocompatible macromolecular block and at least one kind of cell and has voids and in which a plurality of the above-described biocompatible macromolecular blocks are arranged in gaps between a plurality of the above-described cells, in which a ratio of the volume of the above-described biocompatible macromolecular blocks with respect to the volume of the above-described cell structure is 10% to 30%, a ratio of the volume of the above-described cells with respect to the volume of the above-described cell structure is 20% to 50%, and a ratio of the volume of the above-described void with respect to the volume of the above-described cell structure is 35% to 60%.

(2) The cell structure according to (1), in which the above-described cells include at least human mesenchymal stem cells.
(3) The cell structure according to (1) or (2), in which the above-described cells include at least vascular cells.
(4) The cell structure according to any one of (1) to (3) which is used for cell transplantation.
(5) The cell structure according to (4) which is used for cell transplantation into the renal capsule.
(6) The cell structure according to any one of (1) to (5), in which the size of one of the above-described biocompatible macromolecular blocks is 10 μm to 300 μm.
(7) The cell structure according to any one of (1) to (6), in which the thickness or the diameter is 400 μm to 3 cm.
(8) The cell structure according to any one of (1) to (7), in which the above-described biocompatible macromolecular block consists of a recombinant peptide.
(9) The cell structure according to (8), in which the above-described recombinant peptide is any of a peptide formed of an amino acid sequence described in SEQ ID No: 1, a peptide which consists of an amino acid sequence in which one or a plurality of amino acids are deleted, substituted, or added in the amino acid sequence described in SEQ ID No: 1, and has biocompatibility, or a peptide which consists of an amino acid sequence having 80% or more sequence identity to the amino acid sequence described in SEQ ID No: 1, and has biocompatibility.
(10) The cell structure according to any one of (1) to (9), in which, in the above-described biocompatible macromolecular block, the above-described biocompatible macromolecules are cross-linked using heat, ultraviolet rays, or enzymes.
(11) The cell structure according to any one of (1) to (10), in which the above-described biocompatible macromolecular block is a biocompatible macromolecular block produced through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and a step (b) of freeze-drying the frozen biocompatible macromolecules which have been obtained in the above-described step (a).
(12) The cell structure according to any one of (1) to (11), in which the above-described biocompatible macromolecular block is a biocompatible macromolecular block produced through a method including the step (a) of freezing the solution of the biocompatible macromolecules through the freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, the step (b) of freeze-drying the frozen biocompatible macromolecules which have been obtained in the above-described step (a), and a step (c) of grinding a porous body which has been obtained in the step (b).
(13) The cell structure according to any one of (1) to (12), in which blood vessels are formed inside the above-described cell structure.
(14) A method for producing the cell structure according to any one of (1) to (13), the method comprising: a step of mixing at least one kind of cell with the biocompatible macromolecular block produced through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and a step (b) of freeze-drying the frozen biocompatible macromolecules which have been obtained in the above-described step (a).
(15) A cell structure obtained by merging a plurality of the cell structures according to any one of (1) to (13), with each other.

According to the present invention, the following inventions are further provided.
(16) A cell transplantation method comprising a step of transplanting the cell structure according to any one of (1) to (13) or (15) into a patient who requires cell transplantation.
(17) The cell transplantation method according to (16), in which the cell structure is transplanted into the renal capsule.
(18) Use of the cell structure according to any one of (1) to (13) or (15) for producing a cell transplantation treatment agent.
(19) The use according to (18), in which the cell transplantation treatment agent is a cell transplantation treatment agent transplanted into the renal capsule.
(20) A cell transplantation treatment agent comprising the cell structure according to any one of (1) to (13) or (15).
(21) The cell transplantation treatment agent according to (20) which is a cell transplantation treatment agent transplanted into the renal capsule.

The cell structure of the present invention can be produced without using glutaraldehyde, and therefore, can be used for safe cell transplantation treatment for human bodies. In addition, according to the cell structure of the present invention, it is possible to efficiently form blood vessels after the transplantation.

DESCRIPTION OF THE PREFERRED EMBODIMENTS

Figure 1:
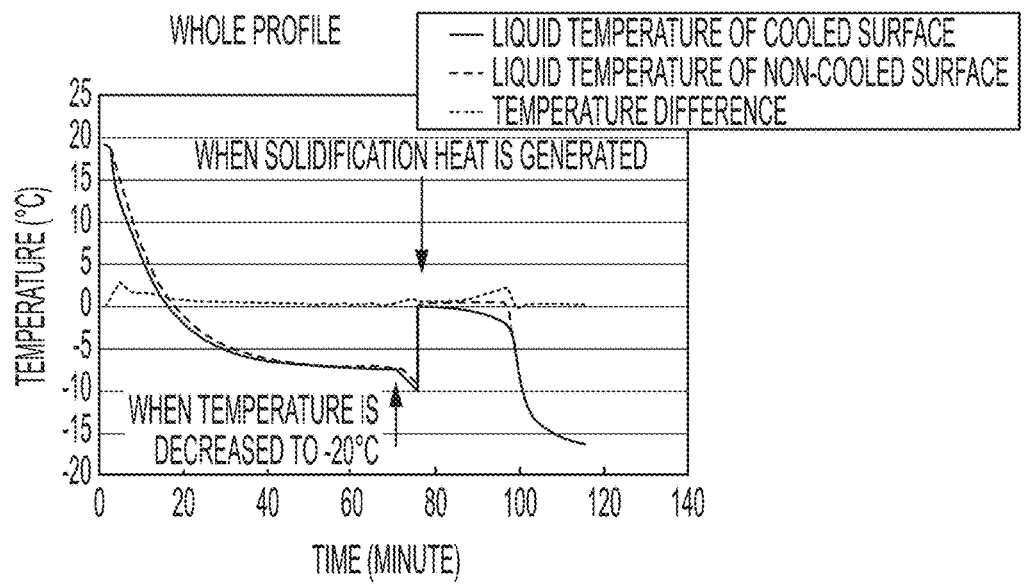
FIG. 1 shows a temperature profile when freezing a solvent under a condition A in Examples.

Hereinafter, an embodiment of the present invention will be described in detail.

The present invention relates to a cell structure which contains a biocompatible macromolecular block and at least one kind of cell and has voids and in which a plurality of the above-described biocompatible macromolecular blocks are arranged in gaps between a plurality of the above-described cells, in which a ratio of the volume of the above-described biocompatible macromolecular blocks with respect to the volume of the above-described cell structure is 10% to 30%, a ratio of the volume of the above-described cells with respect to the volume of the above-described cell structure is 20% to 50%, and a ratio of the volume of the above-described void with respect to the volume of the above-described cell structure is 35% to 60%. In the present specification, in some cases, the cell structure of the present invention is also referred to as a mosaic cell aggregation (a cell aggregation in a mosaic shape).

The ratio of the volume of the biocompatible macromolecular blocks with respect to the volume of the cell structure is 10% to 30%, more preferably 12% to 27%, and particularly preferably 15% to 24%. The ratio of the volume of the cells with respect to the volume of the cell structure is 20% to 50%, more preferably 25% to 45%, and particularly preferably 28% to 42%. The ratio of the volume of the voids with respect to the volume of the cell structure is 35% to 60% and more preferably 35% to 57%. By respectively setting the proportions of the biocompatible macromolecular blocks, the cells, and the voids to be within the above-described ranges, it is possible to form blood vessels in the cell structure.

The ratio of the volume of the biocompatible macromolecular blocks, the ratio of the volume of the cells, and the ratio of the volume of the voids, with respect to the volume of the cell structure can be obtained through the following method.

An image in which the entirety of a cell structure comes within the field of vision is prepared. An image obtained by extracting only biocompatible macromolecular blocks from the image using image extraction software such as photoshop (registered trademark) and an image obtained by extracting only cells from the image are prepared. In these extracted images, the area occupied by the entirety of the cell structure (mosaic cell aggregation), the area occupied by the biocompatible macromolecular blocks, and the area occupied by the cells are calculated using image software such as Imagej (registered trademark). The ratio of the area occupied by the biocompatible macromolecular blocks with respect to the area occupied by the entirety of the cell structure (mosaic cell aggregation) is regarded as the ratio of the volume of the biocompatible macromolecular blocks with respect to the volume of the cell structure, and the ratio of the area occupied by the cells with respect to the area occupied by the entirety of the cell structure (mosaic cell aggregation) is regarded as the ratio of the volume of the cells with respect to the volume of the cell structure. The ratio of the volume of the voids is calculated as "ratio of volume of void=ratio (100%) of volume of cell structure−ratio of volume of biocompatible macromolecular blocks−ratio of volume of cells". That is, the voids referred to in the present invention mean a space other than a space occupied by the biocompatible macromolecular blocks and a space occupied by the cells, out of a space occupied by the cell structure.

(1) Biocompatible Macromolecular Blocks (1-1) Biocompatible Macromolecules

Biocompatibility means a property which does not cause a significantly harmful reaction such as a long-term and chronic inflammatory reaction, during contact with a living body. Whether or not the biocompatible macromolecules used in the present invention are decomposed within a living body is not particularly limited as long as the biocompatible macromolecules have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of the biodegradable materials include polypeptide (for example, gelatin or the like to be described below) such as recombinant peptide, polylactic acid, polyglycolic acid, lactic acid-glycolic acid copolymers (PLGA), hyaluronic acid, glycosaminoglycan, proteoglycan, chondroitin, cellulose, agarose, carboxymethyl cellulose, chitin, and chitosan. Among these, recombinant peptide is particularly preferable. Devising of an improvement of cell adhesion properties in these biocompatible macromolecules may be performed. Specifically, methods such as "coating of the surface of a base material with a cell adhesion substrate (fibronectin, vitronectin, or laminin) or peptides of a cell adhesion sequence (an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, which are represented by one-letter notation of amino acids)", "amination or cationization of the surface of a base material", or "plasma treatment performed on the surface of a base material or hydrophilic treatment due to corona discharge" can be used.

The kinds of polypeptides containing recombinant peptides are not particularly limited as long as polypeptides have biocompatibility. For example, gelatin, collagen, elastin, fibronectin, ProNectin, laminin, tenascin, fibrin, fibroin, entactin, thrombospondin, and RetroNectin are preferable and gelatin, collagen, and atelocollagen are most preferable. As the gelatin to be used in the present invention, natural gelatin or recombinant gelatin is preferable and recombinant gelatin is more preferable. The natural gelatin referred to herein means gelatin produced using naturally derived collagen. The recombinant gelatin will be described below in the present specification.

A "1/IOB" value which is a hydrophilic value of biocompatible macromolecules used in the present invention is preferably within a range of 0 to 1.0, more preferably within a range of 0 to 0.6, and still more preferably within a range of 0 to 0.4. IOB is an index of hydrophilic and hydrophobic properties based on an organic conceptual diagram representing polarity and non-polarity of an organic compound proposed by Atsushi HUJITA, and the details thereof are described in, for example, "Pharmaceutical Bulletin", vol. 2, 2, pp. 163-173 (1954), "Area of Chemistry" vol. 11, 10, pp. 719-725 (1957), and "Fragrance Journal, vol. 50, pp. 79-82 (1981). Briefly, the root of every organic compound is set to methane ($CH_4$), and all of other compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is shown on the X-axis and the inorganic value is shown on the Y-axis. IOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram—Foundation and Application-" (written by Yoshio KOUDA, Sankyo Shuppan Co., Ltd., 2008). In the present specification, the hydrophilic and hydrophobic properties are represented by a "1/IOB" value which was obtained by taking a reciprocal number of JOB. This is a notation of representing more hydrophilic properties as the "1/IOB" value becomes small (close to 0).

The hydrophilic properties and water absorbency become high by making the "1/IOB" value of the macromolecules used in the present invention be within the above-described range, which effectively acts to hold nutrient components. As a result, it is estimated that this point contributes to stability of cells and easy survival of cells in a cell structure (mosaic cell aggregation) of the present invention.

In a case where the biocompatible macromolecules used in the present invention are polypeptides, the hydrophilic and hydrophobic indexes represented by a grand average of hydropathicity (GRAVY) value is preferably −9.0 to 0.3, and more preferably −7.0 to 0.0. The grand average of hydropathicity (GRAVY) value can be obtained through "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appeal R. D., Bairoch A.; ExPASy: the proteomics server for in-depth protein knowledge and analysis; Nucleic Acids Res. 31:3784-3788 (2003)".

The hydrophilic properties and water absorbency become high by making the GRAVY value of the macromolecules used in the present invention be within the above-described range, which effectively acts to hold nutrient components. As a result, it is estimated that this point contributes to stability of cells and easy survival of cells in a cell structure (mosaic cell aggregation) of the present invention.

(1-2) Cross-Linking

The biocompatible macromolecules used in the present invention may be or may not be cross-linked, but are preferably cross-linked. By using the cross-linked biocompatible macromolecules, it is possible to obtain an effect of preventing instant decomposition during culturing in a medium and during transplantation into a living body. As a general cross-linking method, thermal cross-linking, cross-linking using aldehydes (for example, formaldehyde or glutaraldehyde), cross-linking using a condensation agent (carbodiimide, cyanamide, or the like), enzymatic cross-linking, photocrosslinking, ultraviolet cross-linking, a hydrophobic interaction, hydrogen bonding, an ionic interaction, and the like are known. In the present invention, it is preferable to use a cross-linking method in which glutaraldehyde is not used. In the present invention, it is more preferable to use a cross-linking method in which aldehydes or condensation agents are not used. That is, the biocompatible macromolecular blocks in the present invention are preferably biocompatible macromolecular blocks which do not contain glutaraldehyde, and are more preferably biocompatible macromolecular blocks which do not contain aldehydes or condensation agents. As the cross-linking method used in the present invention, thermal cross-linking, ultraviolet cross-linking, or enzymatic cross-linking is more preferable, and thermal cross-link is particularly preferable.

In a case of performing cross-linking using an enzyme, there is no particular limitation as long as the enzyme has a cross-linking action between macromolecular materials. However, it is possible to perform cross-linking preferably using transglutaminase and laccase and most preferably using transglutaminase. Specific examples of protein to be subjected to enzymatic cross-linking using transglutaminase are not particularly limited as long as the protein has a lysine residue and a glutamine residue. Transglutaminase may be derived from a mammal or may be derived from a microorganism. Specific examples thereof include mammal-derived transglutaminase which has been sold as Activa series manufactured by Ajinomoto Co., Inc., and a reagent; guinea pig liver-derived transglutaminase manufactured by, for example, Oriental Yeast Co., Ltd., Upstate USA Inc., or Biodesign International, Inc.; goat-derived transglutaminase; rabbit-derived transglutaminase; and human-derived blood coagulation factors (Factor XIIIa: Haematologic Technologies, Inc).

The reaction temperature when performing cross-linking (for example, thermal cross-linking) is not particularly limited as long as cross-linking can be performed, but is preferably −100° C. to 500° C., more preferably 0° C. to 300° C., still more preferably 50° C. to 300° C., still more preferably 100° C. to 250° C., and still more preferably 120° C. to 200° C.

(1-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently show any amino acids) represented by Gly-X-Y which is characteristic to collagen. Here, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen, and to use recombinant gelatin disclosed in, for example, EP1014176A2, U.S. Pat. No. 6,992,172B, WO2004/85473A, and WO2008/103041A. However, the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. In addition, the recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2 kDa to 100 kDa, more preferably 2.5 kDa to 95 kDa, still more preferably 5 kDa to 90 kDa, and most preferably 10 kDa to 90 kDa.

The recombinant gelatin preferably has a repetition of a sequence represented by Gly-X-Y which is characteristic to collagen. Here, a plurality of pieces of Gly-X-Y may be the same as or different from each other. In Gly-X-Y, Gly represents glycine and X and Y represent an arbitrary amino acid (preferably represents an arbitrary amino acid other than glycine). The sequence represented by Gly-X-Y characteristic to collagen is a partial structure which is extremely specific compared to other protein in a composition or a sequence of an amino acid of gelatin/collagen. In this section, glycine occupies about one third of the entirety of the amino acid sequence, one sequence is repeated every three sequences. Glycine is the simplest amino acid. Therefore, there is a little restraint in arrangement of molecular chains and glycine significantly contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin has a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, or arginine. Among these, the polar non-charged amino acid indicates cysteine, asparagine, glutamine, serine, threonine, or tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is greater than or equal to 5% and less than 20% and preferably less than 10%. Furthermore, it is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, Nagai Shoten Co., Ltd., "Pathophysiology", Vol. 9, No. 7 (1990) p. 527). The recombinant gelatin used in the present invention preferably has two or more these cell adhesion signals in one molecule. As the specific sequences, sequences such as an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, which are represented by one-letter notation of amino acids are preferable in that there are many kinds of cells adhered. An RGD sequence, a YIGSR sequence (SEQ ID NO: 3), a PDSGR sequence (SEQ ID NO: 4), an LGTIPG sequence (SEQ ID NO: 6), an IKVAV sequence (SEQ ID NO: 8), and a HAV sequence are more preferable and an RGD sequence is particularly preferable. In the RGD sequence, an ERGD sequence (SEQ ID NO: 10) is preferable. It is possible to improve the production amount of substrate of a cell using recombinant gelatin having cell adhesion signals. For example, it is possible to improve the production of glycosaminoglycan (GAG) in a case of cartilage differentiation using mesenchymal stem cells as cells.

As arrangement of RGD sequences in recombinant gelatin used in the present invention, it is preferable that the number of amino acids between RGDs is between 0 to 100 and preferably between 25 to 60 without being even.

The content of this minimum amino acid sequence is preferably 3 to 50, more preferably 4 to 30, and particularly preferably 5 to 20 in one molecule of protein in view of cell adhesion properties and proliferation properties. The most preferable content thereof is 12.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs with respect to the total number of amino acids is still more preferably at least 0.6%, still more preferably at least 0.8%, still more preferably at least 1.0%, still more preferably at least 1.2%, and most preferably at least 1.5%. The number of RGD motifs within a recombinant peptides is, per 250 amino acids, preferably at least 4, still more preferably 6, still more preferably 8, and still more preferably 12 to 16. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin of the present invention contains at least two RGD sequences per 250 amino acids, more preferably contains at least three RGD sequences per 250 amino acids, and still more preferably contains at least four RGD sequences per 250 amino acids. As a further mode of the recombinant gelatin of the present invention, the recombinant gelatin contains at least four RGD motifs, preferably 6 RGD motifs, more preferably 8 RGD motifs, and still more preferably 12 to 16 RGD motifs.

In addition, the recombinant gelatin may be partially hydrolyzed.

The recombinant gelatin used in the present invention is preferably represented by Formula: A-[(Gly-X-Y)$_n$]$_m$-B. n pieces of X each independently represent any amino acid and n pieces of Y each independently represent any amino acid. m is preferably 2 to 10 and more preferably 3 to 5. n is preferably 3 to 100, more preferably 15 to 70, and most preferably 50 to 65. A represents an arbitrary amino acid or an amino acid sequence, B represents an arbitrary amino acid or an amino acid sequence, n pieces of X each independently represent any amino acid, and n pieces of Y each independently represent any amino acid.

More preferably, the recombinant gelatin used in the present invention is represented by Formula: Gly-Ala-Pro-[(Gly-X-Y)63]3-Gly (where 63 pieces of X each independently represent any amino acid and 63 pieces of Y each independently represent any amino acid. 63 pieces of Gly-X-Y may be the same as or different from each other) (SEQ ID NO: 11).

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen, and more preferably I type collagen, II type collagen, or III type collagen. According to another form, the above-described collagen is preferably derived from a human, cattle, a pig, a mouse, or a rat, and is more preferably derived from a human.

An isoelectric point of the recombinant gelatin used in the present invention is preferably 5 to 10, more preferably 6 to 10, and still more preferably 7 to 9.5.

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of
(1) a peptide formed of an amino acid sequence described in SEQ ID No: 1;
(2) a peptide which consists of an amino acid sequence in which one or a plurality of amino acids are deleted, substituted, or added in the amino acid sequence described in SEQ ID No: 1, and has biocompatibility; or
(3) a peptide which consists of an amino acid sequence having 80% or more (more preferably 90% or more, particularly preferably 95% or more, and most preferably 98% or more) sequence identity to the amino acid sequence described in SEQ ID No: 1, and has biocompatibility.

"One or a plurality of" in the "amino acid sequence in which one or a plurality of amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/85473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(1-4) Biocompatible Macromolecular Block

In the present invention, a block (aggregation) consisting of the above-described biocompatible macromolecules is used.

The shape of the biocompatible macromolecular block in the present invention is not particularly limited. Examples thereof include an amorphous shape, a spherical shape, a particulate shape, a powdery shape, a porous shape, a fibrous shape, a spindle shape, a flat shape, and a sheet shape. An amorphous shape, a spherical shape, a particulate shape, a powdery shape, and a porous shape are preferable and an amorphous shape is more preferable. The amorphous shape indicates that the shape of a surface is uneven, and indicates, for example, an object, such as rock, which has roughness.

The size of one biocompatible macromolecular block in the present invention is not particularly limited, but is preferably 1 μm to 700 μm, more preferably 10 μm to 700 μm, still more preferably 10 μm to 300 μm, still more preferably 20 μm to 200 μm, still more preferably 20 μm to 150 μm, and particularly preferably 25 μm to 106 μm. It is possible to achieve more excellent angiogenesis by setting the size of one biocompatible macromolecular block to be within the above-described range. The size of one biocompatible macromolecular block does not mean that an average value of the sizes of a plurality of biocompatible macromolecular blocks is within the above-described range, but means the size of each biocompatible macromolecular block which is obtained by sieving a plurality of biocompatible macromolecular blocks.

The size of one block can be defined by the size of a sieve used when dividing the block. For example, blocks remaining on a sieve with 106 μm when blocks which have been passed through a sieve with 180 μm for sifting are sifted using the sieve with 106 μm can be regarded as blocks having a size of 106 to 180 μm. Next, blocks remaining on a sieve with 53 μm when blocks which have been passed through the sieve with 106 μm for sifting are sifted using the sieve with 53 μm can be regarded as blocks having a size of 53 to 106 μm. Next, blocks remaining on a sieve with 25 μm when blocks which have been passed through the sieve with 53 μm for sifting are sifted using the sieve with 25 μm can be regarded as blocks having a size of 25 to 53 μm.

(1-5) Method for Producing Biocompatible Macromolecular Block

The method for producing a biocompatible macromolecular block is not particularly limited. For example, it is possible to obtain a biocompatible macromolecular block by grinding a porous body of biocompatible macromolecules using a grinder (such as new PowerMILL).

When producing a porous body of biocompatible macromolecules, shape of ice to be formed becomes a spherical shape due to inclusion of a freezing step in which the liquid temperature (highest internal liquid temperature) in a portion having the highest liquid temperature within a solution becomes lower than or equal to a "melting point of a solvent −3° C." in an unfrozen state. A porous body having spherical isotropic hollow holes (spherical holes) is obtained when the ice is dried through this step. The shape of the ice to be formed becomes a columnar or tabular shape when the ice is frozen without including a freezing step in which the liquid temperature (highest internal liquid temperature) in a portion having the highest liquid temperature within a solution becomes higher than or equal to a "melting point of a solvent—3° C." in an unfrozen state. A porous body having columnar or tabular hollow holes (columnar or tabular holes) which are uniaxially or biaxially long is obtained when the ice is dried through this step.

In the present invention, it is preferable that it is possible to produce biocompatible macromolecular blocks through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature (a "melting point of a solvent—3° C.") which is 3° C. lower than a melting point of a solvent in an unfrozen state; and a step (b) of freeze-drying the frozen biocompatible macromolecules which have been obtained in the above-described step (a).

In the present invention, it is more preferable that it is possible to produce biocompatible macromolecular blocks by grinding the porous body obtained in the above-described step (b).

It is more preferable that it is possible to freeze the solution of the biocompatible macromolecules through freezing treatment in which the highest internal liquid temperature, which is a liquid temperature in a portion having the highest liquid temperature within the solution, becomes lower than or equal to a temperature (a "melting point of a solvent—7° C.") which is 7° C. lower than a melting point of a solvent in an unfrozen state, in the above-described step (a).

(2) Cells

As cells used in the present invention, it is possible to use arbitrary cells as long as cell transplantation for the purpose of a cell structure of the present invention can be performed, and the kinds thereof are not particularly limited. In addition, one kind of cell may be used or a plurality of kinds of cells may be used in combination. In addition, cells to be used are preferably animal cells, more preferably vertebrate animal-derived cells, and particularly preferably human-derived cells. The kinds of vertebrate animal-derived cells (particularly human-derived cells) may be either of pluripotent cells, somatic stem cells, precursor cells, and mature cells. As the pluripotent cells, it is possible to use, for example, embryonic stem (ES) cells, germline stem (GS) cells, or induced pluripotent stem (iPS) cells. As the somatic stem cells, it is possible to use, for example, mesenchymal stem cells (MSC), hematopoietic stem cells, amniotic cells, cord blood cells, bone marrow-derived cells, cardiac muscle stem cells, adipose-derived stem cells, or neural stem cells. As the precursor cells and mature cells, it is possible to use, for example, cells derived from the skin, the dermis, the epidermis, muscles, cardiac muscles, nerves, bones, cartilage, the endothelium, the brain, epithelium, the heart, the kidney, the liver, the pancreas, the spleen, the inside of the oral cavity, the cornea, bone marrow, cord blood, amnion, or hair. As the human-derived cells, it is possible to use, for example, ES cells, iPS cells, MSC, chondrocytes, osteoblasts, osteoprogenitor cells, mesenchyme cells, myoblasts, cardiac muscle cells, cardiac myoblasts, nerve cells, liver cells, beta cells, fibroblasts, corneal endothelial cells, vascular endothelial cells, corneal epithelial cells, amniotic cells, cord blood cells, bone marrow-derived cells, or hematopoietic stem cells. In addition, the cells may be derived from any of autologous cells or heterologous cells.

For example, in heart disease such as serious heart failure or serious myocardial infarction it is possible to favorably use myocardial cells, smooth muscle cells, fibroblasts, skeletal muscle-derived cells (particularly satellite cells), bone marrow cells (particularly bone marrow cells that have been differentiated into cardiac muscle-like cells), all of which are removed in autologous and heterologous manners. Furthermore, it is possible to appropriately select transplantation cells even in other organs. Examples of the transplantation include transplantation of nerve precursor cells or cells which can be differentiated into nerve cells, into a cerebral ischemia site or a stroke site, or transplantation of vascular endothelial cells, or cells which can be differentiated into the vascular endothelial cells, into a myocardial infarction site or a skeletal muscle ischemia site.

In addition, examples of the cells include cells used in cell transplantation with respect to diabetic organopathy. Examples thereof include various cells for cell transplantation therapy which have been reviewed, with respect to diseases such as kidney disorders, pancreas disorders, peripheral nerve disorders, eye disorders, and interruption in circulation of the limbs. That is, an attempt of transplanting insulin-secreting cells into the pancreas of which the insulin-secreting ability is deteriorated, transplantation of bone marrow-derived cells with respect to interruption in circulation of the limbs, or the like has been reviewed, and it is possible to use such cells.

In addition, it is possible to use vascular cells. In the present specification, the vascular cells mean cells associated with angiogenesis, and are cells constituting blood vessels and blood, and precursor cells and somatic stem cells which can be differentiated to the cells thereof. Here, pluripotent cells such as ES cells, GS cells, or iPS cells; or cells, such as mesenchymal stem cells (MSC), constituting blood vessels and blood, which are not naturally differentiated are not contained in the vascular cells. As the vascular cells, cells constituting blood vessels are preferable. In the vertebrate animal-derived cells (particularly human-derived cells), specific examples of the cells constituting blood vessels include vascular endothelial cells and vascular smooth muscle cells. As the vascular endothelial cells, any of venous endothelial cells and arterial endothelial cells may be used. As the precursor cells of the vascular endothelial cells, it is possible to use vascular endothelial precursor cells, and to preferably use vascular endothelial cells and vascular endothelial precursor cells. As the cells constituting blood, it is possible to use corpuscle cells. It is possible to use white corpuscle cells such as lymphocytes or neutrophils, monocyte cells, and hematopoietic stem cells which are stem cells thereof.

In the present specification, the non-vascular cells mean cells other than the above-described vascular cells. For example, ES cells, iPS cells, mesenchymal stem cells (MSC), cardiac muscle stem cells, cardiac muscle cells, fibroblasts, myoblasts, chondrocytes, liver cells, or nerve cells can be used. MSC, chondrocytes, myoblasts, cardiac muscle stem cells, cardiac muscle cells, liver cells, or iPS cells can be preferably used. MSC, cardiac muscle stem cells, cardiac muscle cells, or myoblasts are more preferably used.

(3) Cell Structure

In the present invention, the cell structure can have a thickness suitable for cell transplantation by three-dimensionally arranging a plurality of biocompatible macromolecular blocks in gaps between a plurality of cells in a mosaic shape using the biocompatible macromolecular blocks and the cells. Furthermore, a cell structure in which cells evenly exist in the structure is formed by three-dimensionally arranging the biocompatible macromolecular blocks and the cells in a mosaic shape, and it is possible to deliver nutrients to the inside of the cell structure from the outside. Accordingly, it is possible to form blood vessels if cell transplantation is performed using the cell structure of the present invention.

In the cell structure of the present invention, the plurality of biocompatible macromolecular blocks are arranged in gaps between the plurality of cells. Here, the "gaps between cells" is not necessarily a space closed by the constituent cells, and may be interposed by the cells. Gaps are not necessarily present between all of the cells, and there may be a place where cells are brought into contact with each other. The distance of gaps between cells through biocompatible macromolecular blocks, that is, the gap distance when selecting a certain cell, and a cell existing in a shortest distance from the certain cell is not particularly limited. However, the distance is preferably the size of a biocompatible macromolecular block, and a favorable distance is also within the range of the favorable size of a biocompatible macromolecular block.

In addition, the biocompatible macromolecular blocks have a configuration of being interposed by the cells. However, there are not necessarily cells between all of the biocompatible macromolecular blocks, and there may be a place where biocompatible macromolecular blocks are brought into contact with each other. The distance between biocompatible macromolecular blocks through cells, that is, the distance when selecting a biocompatible macromolecular block, and a biocompatible macromolecular block existing in a shortest distance from the biocompatible macromolecular block is not particularly limited. However, the distance is preferably the size of an aggregation of cells when one or several cells to be used are gathered. For example, the size thereof is 10 µm to 1000 µm, preferably 10 µm to 100 µm, and more preferably 10 µm to 50 µm.

The expressions such as "evenly exist", for example, the "cell structure in which cells evenly exist in the structure" is used in the present specification. However, the expression does not mean complete evenness, but means that it is possible to deliver nutrients to the inside of the cell structure from the outside.

The thickness or the diameter of the cell structure of the present invention can be set to a desired thickness. As the lower limit, being greater than or equal to 215 µm is preferable, being greater than or equal to 400 µm is more preferable, and being greater than or equal to 730 µm is most preferable. The upper limit of the thickness or the diameter is not particularly limited, but a general range in use is preferably less than or equal to 3 cm, more preferably less than or equal to 2 cm, and still more preferably less than or equal to 1 cm. In addition, the range of the thickness or the diameter of the cell structure is preferably 400 µm to 3 cm, more preferably 500 µm to 2 cm, and still more preferably 720 µm to 1 cm. By setting the thickness or the diameter of the cell structure to be within the above-described range, it is possible to further promote angiogenesis.

In the cell structure of the present invention, a region formed of biocompatible macromolecular blocks and a region formed of cells are preferably arranged in a mosaic shape. The "thickness or the diameter of cell structure" in the present specification indicates the following. When selecting a certain point A in the cell structure, the length of a line segment which divides the cell structure is set as a line segment A such that the distance from the external boundary of the cell structure becomes shortest within a straight line passing through the point A. A point A at which the line segment A thereof in the cell structure becomes longest is selected, and the length of the line segment A during the selection thereof is set as the "length or the diameter of the cell structure".

In the cell structure of the present invention, the ratio of a biocompatible macromolecular block to a cell is not particularly limited. However, the ratio of a biocompatible macromolecular block per cell is preferably 0.0000001 µg to 1 µg, more preferably 0.000001 µg to 0.1 µg, still more preferably 0.00001 µg to 0.01 µg, and most preferably 0.00002 µg to 0.006 µg. By setting the ratio of the biocompatible macromolecular block to the cell to be within the above-described range, it is possible to make the cells more evenly exist. In addition, it is possible to make the ratio of the volume of the biocompatible macromolecular blocks with respect to the volume of the cell structure and the ratio of the volume of the cells with respect to the volume of the cell structure be within the range defined in the present invention. By setting the lower limit to be within the above-described range, it is possible to exhibit an effect of the cells when using the cells for the above-described purpose. Moreover, by setting the upper limit to be within the above-described range, it is possible to supply components in arbitrarily existing biocompatible macromolecular blocks to cells. Here, the components in biocompatible macromolecular blocks are not particularly limited, but examples thereof include components contained in a medium to be described below.

In addition, the cell structure of the present invention may contain an angiogenic factor. Here, examples of the angiogenic factor favorably include a basic fibroblast growth factor (bFGF), a vascular endothelial growth factor (VEGF), and a hepatocyte growth factor (HGF). The method for producing a cell structure containing an angiogenic factor is not particularly limited, but examples thereof include a production method using biocompatible macromolecular blocks in which an angiogenic factor is impregnated. It is preferable that the cell structure of the present invention contains an angiogenic factor from the viewpoint of promoting angiogenesis.

The cell structure of the present invention may contain non-vascular cells. In addition, cells constituting the cell structure of the present invention may be only non-vascular cells. It is possible to form blood vessels in a transplantation site after the transplantation using the cell structure of the present invention which contains only non-vascular cells as cells. In addition, in a case where the cells constituting the cell structure of the present invention are two or more kinds and include both of non-vascular cells and vascular cells, it is possible to form more blood vessels compared to the case where the cell structure is constituted only non-vascular cells, which is preferable.

A cell structure in which blood vessels are formed is preferable as the cell structure of the present invention.

A cell structure in which blood vessels are formed using the cell structure of the present invention which contains two or more kinds of cells and contains both non-vascular cells and vascular cells is also included in the cell structure of the present invention. Here, the favorable range of the "cell structure of the present invention which contains two or more kinds of cells and contains both non-vascular cells and vascular cells" is the same as that described above.

(4) Method for Producing Cell Structure

The cell structure of the present invention can be produced by mixing a biocompatible macromolecular block with at least one kind of cell. More specifically, the cell structure of the present invention can be produced by alternately arranging a biocompatible macromolecular block and a cell. The production method is not particularly limited, but a method for sowing cells after forming a biocompatible macromolecular block is preferably used. Specifically, it is possible to produce the cell structure of the present invention by incubating a mixture of a biocompatible macromolecular block and a cell-containing culture solution. For example, in the solution held by a container, in the container, a cell and the previously produced biocompatible macromolecular block are arranged in a mosaic shape. It is preferable to promote or control the formation of the arrangement, which is formed of a cell and a biocompatible base material, in a mosaic shape, through natural aggregation, natural fall, centrifugation, or agitation as means for the arrangement.

As the container to be used, a container formed of a low-adhesive cell material or a non-adhesive cell material is preferable and a container formed of polystyrene, polypropylene, polyethylene, glass, polycarbonate, or polyethylene terephthalate is more preferable. The shape of the bottom surface of a container is preferably a flat bottom shape, a U-shape, and a V-shape.

In the cell structure (mosaic cell aggregation) obtained through the above-described method, it is possible to produce a cell structure having a desired size through a method, for example, (a) merging cell structures (mosaic cell aggregations), which have been separately prepared, with each other, or (b) increasing the volume of the structure under a differentiation medium or a proliferation medium.

The method for merging the cell structures with each other or the method for increasing the volume of the cell structure is not particularly limited.

For example, it is possible to increase the volume of the cell structure by exchanging a medium with a differentiation medium or a proliferation medium in a step of incubating a mixture of a biocompatible macromolecular block and a cell-containing culture solution. Preferably, it is possible to produce a cell structure in which cells evenly exist in the cell structure and which has a desired size, by further adding a biocompatible macromolecular block, in the step of incubating a mixture of a biocompatible macromolecular block and a cell-containing culture solution.

In a case where cell structures which have been separately prepared are merged with each other, it is possible to, for example, merge a plurality of cell structures which contains a plurality of biocompatible macromolecular blocks and a plurality of cells and in which one or a plurality of the above-described biocompatible macromolecular blocks are arranged in some or all of a plurality of gaps formed by the plurality of the above-described cells. A cell structure obtained by merging a plurality of cell structures of the present invention with each other as described in the above-described (a) is also within the scope of the present invention.

Favorable ranges of the "(kinds, sizes, or the like) of biocompatible macromolecular blocks", the "cells", the "gaps between the cells", the "(size or the like) of the obtained cell structure", the "ratio of the cells to the biocompatible macromolecular blocks", and the like according to the method for producing a cell structure of the present invention are the same as those described above in the present specification.

The thickness or the diameter of each cell structure before the above-described merging is preferably 10 µm to 1 cm, more preferably 10 µm to 2000 µm, still more preferably 15 µm to 1500 µm, and most preferably 20 µm to 1300 µm. The thickness or the diameter thereof after the merging is preferably 400 µm to 3 cm, more preferably 500 µm to 2 cm, and still more preferably 720 µm to 1 cm.

Specific examples of the above-described method for producing a cell structure having a desired size by further adding a biocompatible macromolecular block include a method for performing incubating after further adding a second biocompatible macromolecular block to a cell structure which contains a plurality of first biocompatible macromolecular blocks and a plurality of cells and in which one or a plurality of the above-described biocompatible macromolecular blocks are arranged in some or all of a plurality of gaps formed by the plurality of the above-described cells. Here, favorable ranges of the "(kinds, sizes, or the like) of biocompatible macromolecular blocks", the "cells", the "gaps between the cells", the "(size or the like) of the obtained cell structure", the "ratio of the cells to the biocompatible macromolecular blocks", and the like are the same as those described above in the present specification.

Cell structures which need to be merged with each other are preferably installed in a distance of 0 to 50 µm, more preferably installed in a distance of 0 to 20 µm, and still more preferably installed in a distance of 0 to 5 µm. It is considered that, when merging cell structures with each other, cells or a substrate produced by the cells play a role of an adhesive due to proliferation and extension of cells, and the cell structures are bonded to each other. Therefore, it is easy to bond the cell structures to each other by making the distance thereof be within the above-described range.

The range of the thickness or the diameter of the cell structure obtained through the method for producing a cell structure of the present invention is preferably 400 µm to 3 cm, more preferably 500 µm to 2 cm, and still more preferably 720 µm to 1 cm.

It is preferable to appropriately select pace for further adding a second biocompatible macromolecular block to a cell structure when performing incubating after further adding the second biocompatible macromolecular block to the cell structure in accordance with the proliferation rate of cells to be used. Specifically, if the pace for adding a second biocompatible macromolecular block is fast, cells move to the outside of a cell structure, and therefore, the evenness of the cells is deteriorated. If the pace for adding the second biocompatible macromolecular block is slow, a place in which the proportion of cells is increased can be generated, and therefore, evenness of the cells is deteriorated. Thus, the pace is selected in consideration of the proliferation rate of cells to be used.

Favorable examples of the method for producing a cell structure in a case of containing both of the non-vascular cells and vascular cells include the following production methods (a) to (c).

(a) is a production method including a step of adding a vascular cell and a biocompatible macromolecular block after forming a cell structure through the above-described method using a non-vascular cell. Here, the "step of adding a vascular cell and a biocompatible macromolecular block" includes all of the above-described method for merging cell structures (mosaic cell aggregations), which have been prepared, with each other and the above-described method for increasing the volume of the structure under a differentiation medium or a proliferation medium.

(b) is a production method including a step of adding a non-vascular cell and a biocompatible macromolecular block after forming a cell structure through the above-described method using a vascular cell. Here, the "step of adding a non-vascular cell and a biocompatible macromolecular block" includes all of the above-described method for merging cell structures (mosaic cell aggregations), which have been prepared, with each other and the above-described method for increasing the volume of the structure under a differentiation medium or a proliferation medium.

(c) is a production method in which a cell structure is formed through the above-described method using non-vascular cells and vascular cells substantially at the same time.

(5) Application of Cell Structure

The cell structure of the present invention can be used for cell transplantation. Specifically, the cell structure of the present invention can be used for the purpose of, for example, cell transplantation in a heart disease site caused by serious heart failure, serious myocardial infarction, or the like, or in a disease site caused by cerebral ischemia or stroke. In addition, it is also possible to use the cell structure of the present invention for diseases such as diabetic renal disorders, pancreas disorders, peripheral nerve disorders, eye disorders, and interruption in circulation of the limbs.

The cell structure of the present invention can be particularly preferably used for cell transplantation into the renal capsule. Using the cell structure of the present invention, it is possible to form blood vessels within a living body and also to maintain the formed blood vessels within the living body for a long period of time. The cell transplantation into the renal capsule is one of the preferred aspects of the present invention in that it is possible to maintain the formed blood vessels for a particularly long period of time in a case where the cell structure of the present invention is transplanted into the renal capsule.

As the transplantation method, it is possible to use a method using incision, injection, or an endoscope. In the cell structure of the present invention, it is possible to reduce the size of the structure unlike a cell-transplanted substance such as a cell sheet, and therefore, it is possible to perform less invasive transplantation method such as transplantation performed through injection.

In addition, according to the present invention, there is provided a cell transplantation method including a step of transplanting the cell structure of the present invention into a patient who requires cell transplantation. The cell structure of the present invention described above is used in the cell transplantation method of the present invention. The cell structure is preferably transplanted into the renal capsule. The favorable range of the cell structure is the same as that described above.

Furthermore, according to the present invention, use of the cell structure of the present invention for producing a cell transplantation treatment agent is provided. According to the present invention, the use of the cell structure of the present invention is preferably provided in order to produce a cell transplantation treatment agent to be transplanted into the renal capsule. The favorable range of the cell structure is the same as that described above.

Furthermore, according to the present invention, a cell transplantation treatment agent containing the cell structure of the present invention is provided. According to the present invention, the cell transplantation treatment agent which contains the cell structure of the present invention and is transplanted into the renal capsule is preferably provided. The favorable range of the cell structure is the same as that described above.

The present invention will be more specifically described using the following Examples, but is not limited by Examples.

EXAMPLE

[Example 1] Recombinant Peptide (Recombinant Gelatin)

CBE3 (which is disclosed in WO2008/103041A) described in the following was prepared as recombinant peptides (recombinant gelatin).
CBE3:
Molecular weight: 51.6 kD
Structure: GAP[(GXY)$_{63}$]$_3$G (SEQ ID NO: 11)
Number of amino acids: 571
RGD sequence: 12
Imino acid content: 33%

Almost 100% of amino acids have a repeating structure of GXY. In the amino acid sequence of CBE3, serine, threonine, asparagine, tyrosine, and cysteine are not included. CBE3 has an ERGD (SEQ ID NO: 10) sequence.
Isoelectric point: 9.34
GRAVY value: −0.682
1/IOB value: 0.323

Amino acid sequence (SEQ ID No: 1 in a sequence table) (which is the same as that of SEQ ID No: 3 in WO2008/103041A. However, X in the end is corrected to "P").

```
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G
```

[Example 2] Production of Porous Body of Recombinant Peptide

PTFE Thickness•Cylindrical Container

A cylindrical cup-shaped polytetrafluoroethylene (PTFE) container with a bottom surface thickness of 3 mm, a diameter of 51 mm, a side surface thickness of 8 mm, and a height of 25 mm was prepared. When the curved surface of the cylindrical cup-shaped PTFE container is set as a side surface, the side surface of the container is closed by PTFE with 8 mm and the bottom surface (circular shape of a flat plate) is also closed by PTFE with 3 mm. In contrast, the upper surface is in an open shape. Accordingly, the inner diameter of the cylindrical cup-shaped container is set to 43 mm. Hereinafter, this container is referred to as a PTFE thickness•cylindrical container.

[Aluminum Glass•Cylindrical Container]

A cylindrical cup-shaped aluminum container with a thickness of 1 mm and a diameter of 47 mm was prepared. When the curved surface of the cylindrical cup-shaped container is set as a side surface, the side surface of the container is closed by aluminum with 1 mm and the bottom surface (circular shape of a flat plate) is also closed by aluminum with 1 mm. In contrast, the upper surface is in an open shape. In addition, Teflon (registered trademark) with a thickness of 1 mm was evenly spread over only the inside of the side surface, and as a result, the inner diameter of the cylindrical cup became 45 mm. In addition, the bottom surface of this container is in a state in which a glass plate with 2.2 mm was adhered to the outside of aluminum. Hereinafter, this container is called an aluminum glass•cylindrical container.

An aqueous CBE3 solution was made to flow into a PTFE thickness•cylindrical container and an aluminum glass•cylindrical container and was cooled down from the bottom surface within a vacuum freeze dryer (TF5-85ATNNN: Takara Co., Ltd.) using a cooling shelf. A combination of settings for the container, the final concentration of the aqueous CBE3 solution, the liquid amount, and the temperature of the shelf at that time was prepared as described below.

Condition A:

An aqueous CBE3 solution was made to flow into a PTFE thickness•cylindrical container and was cooled down from the bottom surface within a vacuum freeze dryer (TF5-85ATNNN: Takara Co., Ltd.) using a cooling shelf. The PTFE thickness•cylindrical container was used, the final concentration of the aqueous CBE3 solution was 4 mass %, and the amount of aqueous solution was 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the obtained frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased (1.9×10$^5$ Pa). Then, the product was taken out of the vacuum freeze dryer. A porous body was obtained as described above.

Conditions B and C:

4 mL of an aqueous CBE3 solution was made to flow into an aluminum glass•cylindrical container and was cooled down from the bottom surface within a freezer using a cooling shelf. A combination of settings for the final concentration of the container and the aqueous CBE3 solution, the liquid amount, and the temperature of the shelf at that is time was prepared as described below. In addition, freezing was performed by installing the aqueous CBE3 solution-contained container in a place which had been sufficiently cooled down until the temperature of the shelf reached a previously set temperature.

Condition B;

The aluminum glass•cylindrical container was used, the final concentration of the aqueous CBE3 solution was 4 mass %, and the amount of aqueous solution was 4 mL. An aqueous CBE3 solution-contained aluminum glass•container was placed in a place of which the temperature of a shelf was set to be previously cooled down to −60° C., and freezing was performed while maintaining the temperature of the shelf at −60° C. as it was. Thereafter, freeze-drying was performed on the obtained frozen product to obtain a porous body.

Condition C;

The aluminum glass•cylindrical container was used, the final concentration of the aqueous CBE3 solution was 7.5 mass %, and the amount of aqueous solution was 4 mL. An aqueous CBE3 solution-contained aluminum glass•container was placed in a place of which the temperature of a shelf was set to be previously cooled down to −60° C., and freezing was performed while maintaining the temperature of the shelf at −60° C. as it was. Thereafter, freeze-drying was performed on the obtained frozen product to obtain a porous body.

[Example 3] Measurement of Highest Internal Liquid Temperature in Each Freezing Step Since each of the aqueous solutions are cooled down from the bottom surface when producing porous bodies under the conditions A, B, and C, it is most difficult for the temperature of the surface of water in the center portion of a circle to be cooled down. Accordingly, the portion of the surface of water in the center portion of the circle has the highest liquid temperature within the solution. Therefore, the liquid temperature of the portion of the surface of water in the center portion of the circle was measured. Hereinafter, the liquid temperature in the portion of the surface of water in the center portion of the circle is referred to as the highest internal liquid temperature.

Figure 2:
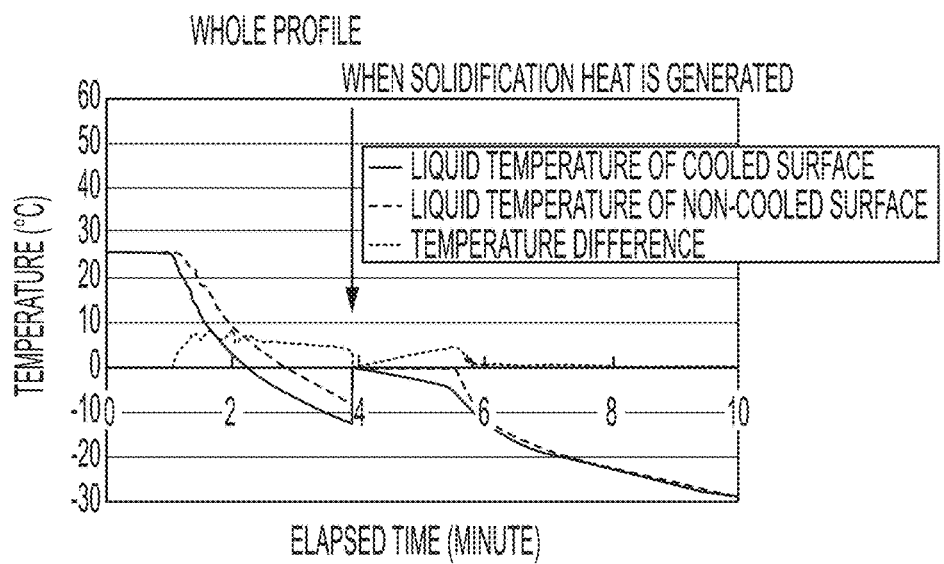
FIG. 2 shows a temperature profile when freezing a solvent under a condition B in Examples.
Figure 3:
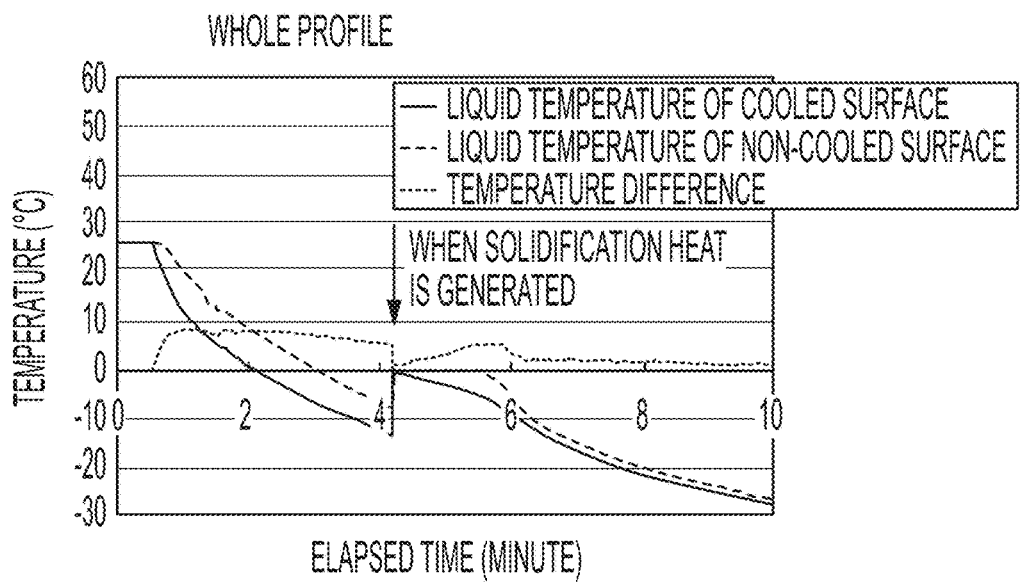
FIG. 3 shows a temperature profile when freezing a solvent under a condition C in Examples.

Temperature profiles with respect to each of the conditions A, B, and C when freezing a solvent are shown in FIGS. 1 to 3. In either case of the conditions A, B, and C, the temperature started to increase due to generation of solidification heat after an unfrozen state at lower than or equal to a melting point, and ice formation actually started in this stage. Thereafter, the temperature was around 0° C. while the certain time passes. In this stage, the product was in a state where there was a mixture of water and ice. The temperature finally started to decrease again from 0° C. In this stage, the liquid portion became ice while being disappeared. The temperature being measured became a solid temperature within the ice, that is, is not the liquid temperature. As described above, whether or not the freezing was performed after the highest internal liquid temperature exceeds a "melting point of a solvent −3° C." in the unfrozen state can be found if the highest internal liquid temperature at the moment when solidification heat is generated is checked.

The highest internal liquid temperature with respect to each of the conditions A, B, and C in the unfrozen state at the moment when solidification heat was generated became −8.8° C. for the condition A, −8.4° C. for the condition B, and −7.2° C. for the condition C. In either case, it can be seen that the highest internal liquid temperature is lower than or equal to the "melting point of a solvent—3° C." in the unfrozen state if the highest internal liquid temperature at the moment when solidification heat is generated is checked.

[Example 4] Production of Recombinant Peptide Block (Grinding and Cross-Linking of Porous Body)

The CBE3 porous body which had been produced under the conditions A, B, or C in Example 2 was ground using new PowerMILL (Osaka Chemical Co., Ltd., new PowerMILL PM-2005). The grinding was performed for one minute×5 times, that is, for 5 minutes in total at the maximum rotation speed. The size of the obtained ground substance was divided using a stainless steel sieve to obtain CBE3 blocks at 25 to 53 μm, 53 to 106 μm, and 106 μm to 180 μm. Thereafter, recombinant peptide blocks were obtained by performing thermal cross-linking (performed for 8 to 48 hours of the cross-linking time) at 160° C. under reduced pressure.

[Comparative Example 1] Production of Simply Frozen Porous Body of Recombinant Peptide A simply frozen porous body of recombinant peptide for comparison was produced as follows as a comparative example according to a method disclosed in JP2014-12114A except that the cross-linking method was changed to thermal cross-linking.

2000 mg of CBE3 was dissolved in 18 mL of ultrapure water at 50° C. to produce 20 mL of a CBE3 solution with a final concentration of 10%. A white plate was put into a silicon frame (about 5 cm×10 cm) which was pressed on the white plate so as not to make an air gap. Thereafter, the above-described CBE3 solution (50° C.) was made to flow into the frame. Thin plate-shaped gel with a thickness of about 4 mm was produced through gelation of about 1 hour while shifting the temperature to 4° C. after the flowing of the solution. After checking the gelation, the temperature was shifted to −80° C. to freeze the gel for 3 hours. After the freezing, freeze-drying was performed using a freeze dryer (EYELA, FDU-1000). The obtained freeze-dried body was a porous body. Hereinafter, this is referred to as a simply frozen porous body.

[Comparative Example 2] Production of Simply Frozen Block of Recombinant Peptide The simply frozen porous body obtained in Comparative Example 1 was ground using new PowerMILL (Osaka Chemical Co., Ltd., new PowerMILL PM-2005). The grinding was performed for one minute×5 times, that is, for 5 minutes in total at the maximum rotation speed. The size of the obtained ground substance was divided using a stainless steel sieve to obtain CBE3 blocks at 25 to 53 μm, 53 to 106 μm, and 106 μm to 180 μm. The obtained CBE3 blocks were thermally cross-linked for 6 to 72 hours after being placed in an oven at 160° C. Hereinafter, these blocks are referred to as simply frozen blocks.

[Example 5] Production of Mosaic Cell Aggregation (hMSC) in which Recombinant Peptide Block is Used Human bone marrow-derived mesenchymal stem cells (hMSC) were adjusted to be $1\times10^5$ cells/mL using a proliferation medium (TAKARA BIO INC.: MSCGM BulletKit (registered trademark)), and CBE3 blocks which had been produced in Example 4 were added thereto so as to make a concentration of 0.1 mg/mL. Then, 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation, which was formed of the CBE3 blocks and hMSC cells and was in a spherical shape with a diameter of 1 mm, was produced. This mosaic cell aggregation contains 0.001 μg of the CBE3 blocks per cell. Since this mosaic cell aggregation was produced in a U-shaped plate, the mosaic cell aggregation was in a spherical shape. Under either of the conditions A, B, and C, and in either of the sizes of the CBE3 blocks of 25 to 53 μm, 53 to 106 μm, and 106 μm to 180 μm, mosaic cell aggregations were similarly obtained.

[Comparative Example 3] Production of Mosaic Cell Aggregation (hMSC) in which Simply Frozen Block of Recombinant Peptide is Used Human bone marrow-derived mesenchymal stem cells (hMSC) were adjusted to be $1\times10^5$ cells/mL using a proliferation medium (TAKARA BIO INC.: MSCGM BulletKit (registered trademark)), and CBE3 blocks which had been produced in Comparative Example 2 were added thereto so as to make a concentration of 0.1 mg/mL. Then, 200 μL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, a mosaic cell aggregation, which was formed of the CBE3 blocks and hMSC cells and was in a spherical shape with a diameter of 1 mm, was produced. This mosaic cell aggregation contains 0.001 μg of the CBE3 blocks per cell. Since this mosaic cell aggregation was produced in a U-shaped plate, the mosaic cell aggregation was in a spherical shape. In either of the sizes of the CBE3 blocks of 25 to 53 μm, 53 to 106 μm, and 106 μm to 180 μm, mosaic cell aggregations were similarly obtained.

[Comparative Example 4] Production of Cell Aggregations (hMSC)

Human bone marrow-derived mesenchymal stem cells (hMSC) were adjusted to be $1\times10^5$ cells/mL or $4\times10^5$ cells/mL using a proliferation medium (TAKARA BIO INC.: MSCGM BulletKit (registered trademark)). Then, 200 μL of the obtained cell suspension was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Accordingly, spherical cell aggregations with a diameter of about 400 μm or 1 mm were produced. A cell aggregation which has been produced at $1\times10^5$ cells/mL is referred to as a small cell aggregation and a cell aggregation which has been produced at $4\times10^5$ cells/mL is referred to as a large cell aggregation.

[Example 6] Analysis of Samples of Present Invention and Comparative Examples Tissue pieces with respect to the mosaic cell aggregation (of which the size of a CBE3 block was 53 to 106 μm) in Example 5, the mosaic cell aggregation (of which the size of a CBE3 block is 53 to 106 μm) in Comparative Example 3, and the large cell aggregation in Comparative Example 4 were produced. Cell aggregations on day 7 of culturing in three examples were used. The mosaic cell aggregation in Example 5, the mosaic cell aggregation in Comparative Example 3, and the large cell aggregation in Comparative Example 4 were immersed into a 10% formalin buffer solution, and formalin fixation was performed. Then, the tissue was embedded by paraffin, and tissue pieces of the cell aggregations were produced. The pieces were subjected to Hematoxylin-Eosin dye (HE dye). The piece images were shown in FIG. 4.

Figure 4:
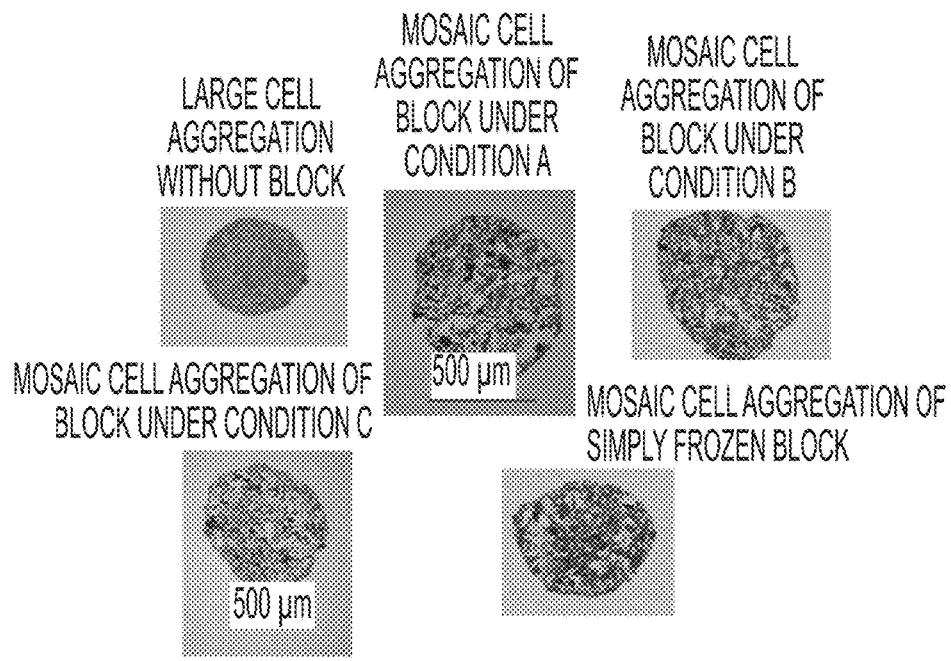
FIG. 4 shows piece images of a mosaic cell aggregation in Example 5, a mosaic cell aggregation in Comparative Example 3, and a large cell aggregation in Comparative Example 4.

The ratio (volume ratio) of biocompatible macromolecular blocks, cells, and voids in each of the mosaic cell aggregation in Example 5, the mosaic cell aggregation in Comparative Example 3, and the large cell aggregation in Comparative Example 4 was obtained using the pieces of the mosaic cell aggregations shown in FIG. 4. A larger proportion of the voids means that material exchange is more easily performed in the mosaic cell aggregations. These values were calculated using image analysis software.

First, an image in which the entirety of a mosaic cell aggregation came within the field of vision was prepared. An image obtained by extracting only biocompatible macromolecular blocks from the image using photoshop (registered trademark) and an image obtained by extracting only cells from the image were prepared. In these extracted images, the area occupied by the entirety of the mosaic cell aggregation, the area occupied by the biocompatible macromolecular blocks, and the area occupied by the cells were calculated using image software Imagej (registered trademark). The ratio of the area occupied by the biocompatible macromolecular blocks with respect to the area occupied by the entirety of the cell structure (mosaic cell aggregation) was regarded as the ratio of the volume of the biocompatible macromolecular blocks with respect to the volume of the cell structure, and the ratio of the area occupied by the cells with respect to the area occupied by the entirety of the cell structure (mosaic cell aggregation) was regarded as the ratio of the volume of the cells with respect to the volume of the cell structure. The ratio of the volume of the voids was calculated as "ratio of volume of void=ratio (100%) of volume of cell structure−ratio of volume of biocompatible macromolecular blocks−ratio of volume of cells".

Measurement results of the volume ratio of biocompatible macromolecular blocks, cells, and voids are shown in Table 1. In the mosaic cell aggregation in Example 5, the proportion of the voids under each of the conditions A, B, and C became 57%, 35%, and 44%. In contrast, the proportion of the voids was 32% in the mosaic cell aggregation in Comparative Example 3. The proportion of the voids was 0% in the cell aggregation in Comparative Example 4 which consisted of only cells. In contrast, the proportion of the biocompatible macromolecular blocks in the mosaic cell aggregation in Example 5 under each of the conditions A, B, and C became 15%, 24%, and 14%. In contrast, the proportion of the biocompatible macromolecular blocks in the mosaic cell aggregation in Comparative Example 3 was 40%. It can be seen that the proportion of the voids in the mosaic cell aggregation in Example 5 is larger than that of the mosaic cell aggregation in Comparative Example 3 and the proportion of the biocompatible macromolecular blocks in the mosaic cell aggregation in Example 5 is smaller than that of the mosaic cell aggregation in Comparative Example 3.

[Table 1]

TABLE 1

Ratio of Block, Cell, and Void in Mosaic Cell Aggregation/Cell Aggregation

| Ratio (%) | Without block (Comparative Example) | Condition A (present invention) | Condition B (present invention) | Condition C (present invention) | Simply frozen (Comparative Example) |
|---|---|---|---|---|---|
| Biocompatible macromolecular block | 0 | 15 | 24 | 14 | 40 |
| Cell | 100 | 28 | 41 | 42 | 28 |
| Void | 0 | 57 | 35 | 44 | 32 |

[Example 7] Production of Mosaic Cell Aggregations (hMSC+hECFC) in which Recombinant Peptide Block is Used and Sample Analysis Human vascular endothelial precursor cells (hECFC) were adjusted to be $1 \times 10^5$ cells/mL using a proliferation medium (LONZA: EGM-2+ECFC serum supplement), and CBE3 blocks which had been produced in Example 5 were added thereto so as to make a concentration of 0.05 mg/mL. Then, 200 μL of the obtained mixture was sown in a Sumilon Celltight X96U plate, and the plate was centrifuged in Mini Plate Centrifuge (600 g, 5 minutes) and was allowed to stand for 24 hours to produce a flat-shaped mosaic cell aggregation formed of hECFC and the CBE3 blocks.

In addition, human bone marrow-derived mesenchymal stem cells (hMSC) were adjusted to be $1 \times 10^5$ cells/mL using a proliferation medium (TAKARA BIO INC.: MSCGM BulletKit (registered trademark)), and CBE3 blocks which had been produced in Example 4 were added thereto so as to make a concentration of 0.1 mg/mL. In this manner, a mixture containing hMSC and the CBE3 blocks was prepared.

The medium was removed from the Sumilon Celltight X96U plate having the flat-shaped mosaic cell aggregation formed of hECFC and the CBE3 blocks, and 200 μL of the above-described mixture containing hMSC and the CBE3 blocks was sown in the above-described Sumilon Celltight X96U plate. The plate was centrifuged in Mini Plate Centrifuge (600 g, 5 minutes) and was allowed to stand for 24 hours to produce a mosaic cell aggregation, which was formed of hMSC, hECFC, and the CBE3 blocks and was in a spherical shape with a diameter of 1 mm.

Under either of the conditions A, B, and C, and in either of the sizes of the CBE3 blocks of 25 to 53 μm, 53 to 106 μm, and 106 μm to 180 μm, mosaic cell aggregations were similarly obtained.

The proportion of the volume regarding the mosaic cell aggregations produced above was calculated from the sample similarly in Example 6. As a result, the proportion of the blocks became 15%, the proportion of the cells became 35%, and the proportion of the voids became 50%.

[Comparative Example 5] Production of Cell Aggregations (hMSC+hECFC)

Human vascular endothelial precursor cells (hECFC) were adjusted to be $1 \times 10^5$ cells/mL using a proliferation medium (LONZA: EGM-2+ECFC serum supplement). 200 μL of the obtained cell suspension was sown in a Sumilon Celltight X96U plate, and the plate was centrifuged in Mini Plate Centrifuge (600 g, 5 minutes) and was allowed to stand for 24 hours to produce a cell aggregation of ECFC.

In addition, human bone marrow-derived mesenchymal stem cells (hMSC) were adjusted to be 300000 cells/mL using a proliferation medium (TAKARA BIO INC.: MSCGM BulletKit (registered trademark)), to produce a cell suspension.

The medium was removed from the Sumilon Celltight X96U plate having the cell aggregation of ECFC, and 200 μL of the cell suspension containing hMSC was sown in the above-described Sumilon Celltight X96U plate. The plate was centrifuged in Mini Plate Centrifuge (600 g, 5 minutes) and was allowed to stand for 24 hours to produce a cell aggregation, which was formed of hMSC and hECFC and was in a spherical shape with a diameter of about 1 mm.

[Example 8] Merging of Mosaic Cell Aggregations (hMSC) in which Recombinant Peptide Block is Used 5 mosaic cell aggregations (using CBE3 blocks of the present invention) on day 2 which had been produced in Example 5 were arranged in a Sumilon Celltight X96U plate, and culturing was performed for 24 hours. As a result, it became clear that the mosaic cell aggregations were naturally merged by bonding cells, which had been disposed at outer peripheral portions between the mosaic cell aggregations, to each other. Under either of the conditions A, B, and C, and in either of the sizes of the CBE3 blocks of 25 to 53 μm, 53 to 106 μm, and 106 μm to 180 μm, the same result was obtained.

[Example 9] Merging of Mosaic Cell Aggregations (hMSC+hECFC) in which Recombinant Peptide Block is Used 5 mosaic cell aggregations (using CBE3 blocks of the present invention) on day 2 which had been produced in Example 7 were arranged in a Sumilon Celltight X96U plate, and culturing was performed for 24 hours. As a result, it became clear that the mosaic cell aggregations were naturally merged by bonding cells, which had been disposed at outer peripheral portions between the mosaic cell aggregations, to each other. Under either of the conditions A, B, and C, and in either of the sizes of the CBE3 blocks of 25 to 53 µm, 53 to 106 µm, and 106 µm to 180 µm, the same result was obtained.

[Comparative Example 6] Merging of Mosaic Cell Aggregations (hMSC) in which Simply Frozen Block of Recombinant Peptide is Used 5 mosaic cell aggregations (using simply frozen blocks of recombinant peptides for comparison) on day 2 which had been produced in Comparative Example 3 were arranged in a Sumilon Celltight X96U plate, and culturing was performed for 24 hours. As a result, it became clear that the mosaic cell aggregations were naturally merged by bonding cells, which had been disposed at outer peripheral portions between the mosaic cell aggregations, to each other. In either of the sizes of the CBE3 blocks of 25 to 53 µm, 53 to 106 µm, and 106 µm to 180 µm, the same result was obtained.

[Comparative Example 7] Merging of Cell Aggregations (hMSC+hECFC)

5 cell aggregations on day 2 which had been produced in Comparative Example 5 were arranged in a Sumilon Celltight X96U plate, and culturing was performed for 24 hours. As a result, it became clear that the cell aggregations were naturally merged by bonding cells, which had been disposed at outer peripheral portions between the cell aggregations, to each other.

Figure 5:
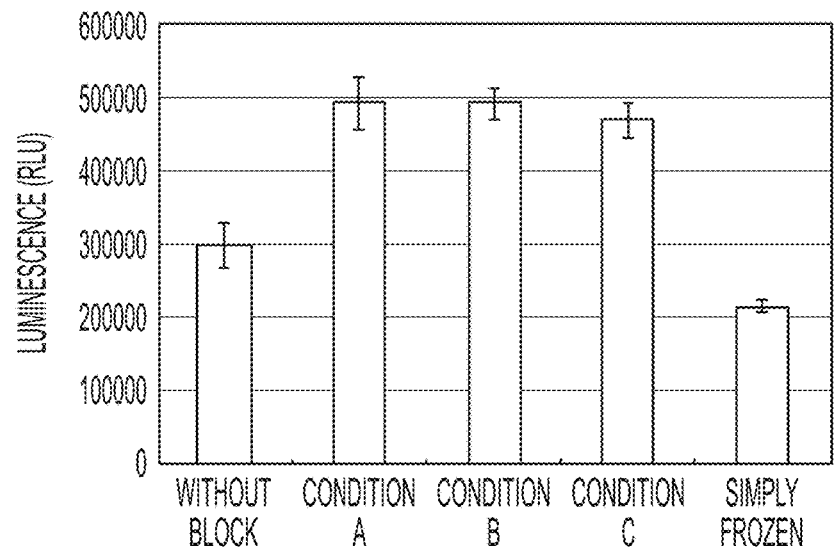
FIG. 5 shows results of ATP assays of mosaic cell aggregations in Example 5 and Comparative Example 3 and the cell aggregation in Comparative Example 4.

[Example 10] In Vitro ATP Assay with Respect to Present Invention and Comparative Examples Regarding the mosaic cell aggregations (three kinds of the conditions A, B, and C; the size of a CBE3 block was 53 to 106 µm) which had been produced in example 5, the mosaic cell aggregation (simply frozen) (of which the size of a CBE3 block was 53 to 106 µm) which had been produced in Comparative Example 3, and the cell aggregation (there is no block) which had been produced in Comparative Example 4, the amount of adenosine triphosphate (ATP) which was generated and held by cells in each mosaic cell aggregation or the cell aggregation was quantitatively determined. ATP is known as an energy source of all living things. By quantitatively determining an ATP synthesis amount and an ATP retention amount, it is possible to grasp a state of a metabolic activity of cells and an activity state of cells. CellTiter-Glo (Promega Corporation) was used for the measurement. Regarding the mosaic cell aggregations produced in Example 5 and Comparative Example 3 and the large cell aggregation produced in Comparative Example 4, and also regarding the cell aggregations on day 7, the ATP amount in each of the mosaic cell aggregations or the cell aggregations was quantitatively determined using CellTiter-Glo. The result showed that the ATP amount was small in the mosaic cell aggregation in Comparative Example 3 compared to that in the mosaic cell aggregation in Example 5 (FIG. 5). In addition, it can be seen that the ATP amount in the large cell aggregation without a biocompatible macromolecular block or voids is small compared to that in the mosaic cell aggregation in Example 3. The original number of cells in the cell aggregation in the Comparative Example 4 is four times the original number of cells in the mosaic cell aggregation in Comparative Example 3. Therefore, the ATP amount in the cell aggregation in Comparative Example 4 is larger than that in the mosaic cell aggregation in Comparative Example 3. From the result shown in FIG. 5, it can be seen that the ATP amount generated by cells in the mosaic cell aggregation in which respective volume proportions of biocompatible macromolecular blocks, cells, and voids are 14% to 24%, 28% to 42%, and 35% to 57% is large.

[Example 11] Dyeing of Live Cells and Dead Cells Using Live Imaging with Respect to Present Invention and Comparative Examples Dyeing of live cells and dead cells in various colors using live imaging was performed using the large cell aggregation and the small cell aggregation in Example 5 (condition A; the size of a CBE3 block is 53 to 106 µm) and Comparative Example 4.

LIVE/DEAD Viability Kit (Life Technology) was used as a dyeing reagent. Live cells and dead cells with respect to mosaic cell aggregations and cell aggregations after 5 days of culturing and after 11 days of culturing were dyed in accordance with the following procedure. The mosaic cell aggregations and the cell aggregations were washed twice using PBS in a U-shaped 96-well plate which had been produced, and were shaded and allowed to stand for 30 minutes at 37° C. in 8 µM Calcein (registered trademark) AM (Life Technology) and 20 µM EthD-1 (Ethidium Homodimer-1; Life Technology). Thereafter, the cell aggregations were observed using a fluorescence microscope at Ex/Em to 495 nm/to 515 nm (green: live cell) and Ex/Em to 495 nm/to 635 nm (red: dead cell).

Figure 6:
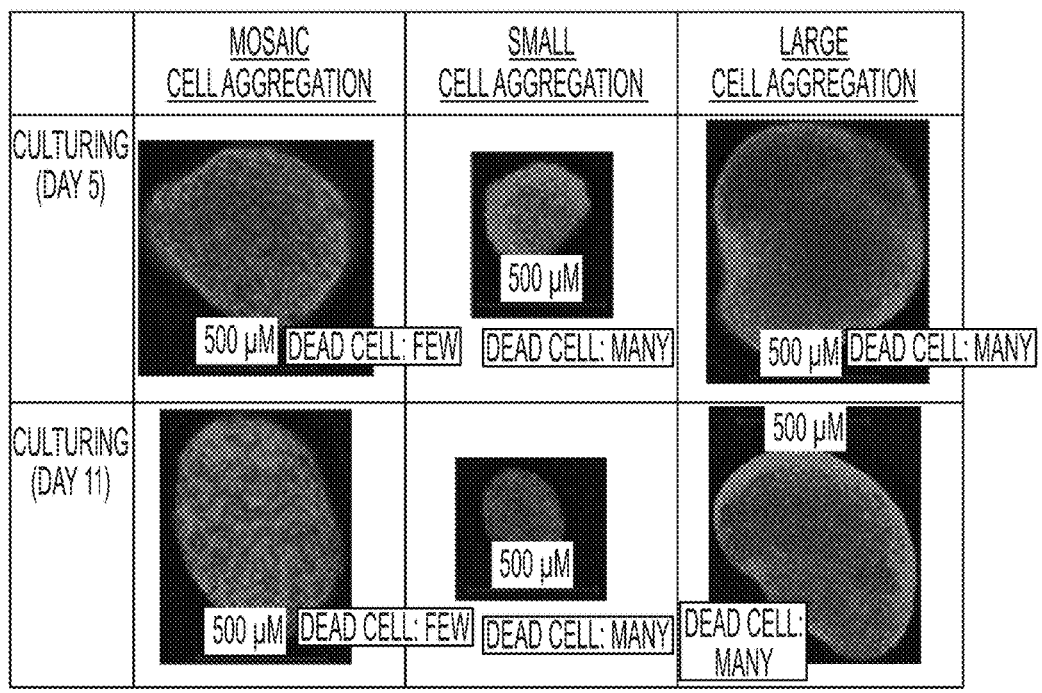
FIG. 6 shows live imaging of live cells and dead cells in the mosaic cell aggregation in Example 5 and the cell aggregation in Comparative Example 4.

The above-described results were shown in FIG. 6. On either of day 5 and day 11 of culturing, it was possible to check that there are few dead cells dyed in red in the mosaic cell aggregation in Example 5 and that many dead cells are scattered in the small cell aggregation and the large cell aggregation in Comparative Example 4. There were few dead cells in the mosaic cell aggregation even in the case of the large cell aggregation having the same size as that of the mosaic cell aggregation and also in the case of the small cell aggregation of which the number of cells is set to be the same as that in the mosaic cell aggregation, in the cell aggregations. This suggests that existence of recombinant peptide blocks and voids makes material exchange such as permeating and feeding of oxygen and nutrients, and discharge of dead cells be easily performed in the mosaic cell aggregation.

[Example 12] Transplanting of Mosaic Cell Aggregation (Under Skin)

A male mouse (at the age of 4 weeks to 6 weeks) of NOD/SCID (Charles River Laboratories International, Inc.) was used as an animal to be transplanted. Body hair of the abdomen of the mouse was removed under anesthesia, a cut was made under the skin of the upper abdomen, forceps are inserted from the cut, and the skin was peeled off from the muscle. Thereafter, the mosaic cell aggregations which had been produced in Examples 8 and 9, and Comparative Example 6 were taken out using forceps and were transplanted under the skin which was near the lower abdomen and was approximately 1.5 cm away from the cut, and the cut portion of the skin was sutured.

Mosaic cell aggregations in which the size of a CBE3 block was 53 to 106 μm under the conditions A, B, and C were used as the mosaic cell aggregations in Example 8, a mosaic cell aggregation in which the size of a CBE3 block was 53 to 106 μm under the condition C was used as the mosaic cell aggregation in Example 9, and a mosaic cell aggregation in which the size of a CBE3 block was 53 to 106 μm was used as the mosaic cell aggregation in Comparative Example 6.

[Example 13] Transplanting of Mosaic Cell Aggregation (Under Renal Capsule)

A male mouse (at the age of 4 weeks to 6 weeks) of NOD/SCID (Charles River Laboratories International, Inc.) was used as an animal to be transplanted. Body hair of the abdomen of the mouse was removed under anesthesia, a cut was longitudinally made in the center portion of the abdomen to open the abdomen, and the internal organs were pulled out to expose the kidneys. The renal capsule of the kidneys was picked up using forceps, and the mosaic cell aggregation in Example 9 and the cell aggregation in Comparative Example 7 were placed between the capsule and parenchyma. Then, the internal organs which have been taken out were returned to the abdomen, and the cut portion was sutured.

A mosaic cell aggregation in which the size of a CBE3 block was 53 to 106 μm under the condition C was used as the mosaic cell aggregation in Example 9.

[Example 14] Collection of Mosaic Cell Aggregation

Dissecting of the mice in which the transplantation was performed in Examples 12 and 13 was performed 1 week, 2 weeks, 4 weeks, and 8 weeks after the transplantation. The skin of the abdomen of each subcutaneously transplanted mice was peeled off and the skin to which the mosaic cell aggregations were adhered was cut off in a square shape with a size of about 1 square cm. In a case where the mosaic cell aggregations were adhered also to the muscle of the abdomen, the muscle was also collected together with the mosaic cell aggregations. The kidneys of the mouse containing the mosaic cell aggregations in which the transplantation was performed under the renal capsule were collected.

[Example 15] Analysis of Samples in Present Invention, Comparative Example, and Reference Example A tissue piece with respect to the skin or the kidneys to which mosaic cell aggregations were adhered was produced. The tissue was immersed into a 4 mass % paraformaldehyde or a 10% formalin buffer solution, and formalin fixation was performed. Then, the tissues were embedded by paraffin, and tissue pieces of the skin containing the mosaic cell aggregations were produced. The pieces were subjected to Hematoxylin-Eosin dye (HE dye) and were used as samples.

Four-stage evaluation was performed on the obtained sample regarding cell survival, angiogenesis, fibrillization, plasma accumulation, and cell death, using a four-point system. In a case where there were a plurality of samples at the same level, an average value thereof was calculated.

In addition, immunological dyeing using kits (for Universal K0673 of a Dako LSAB2 kit and for a dual rabbit•mouse primary antibody of Dako LSAB2 kit/HRP (DAB)) in which DAB color development was used in a CD31 antibody (EPT Anti CD31/PECAM-1) for hECFC dyeing was performed.

Figure 7:
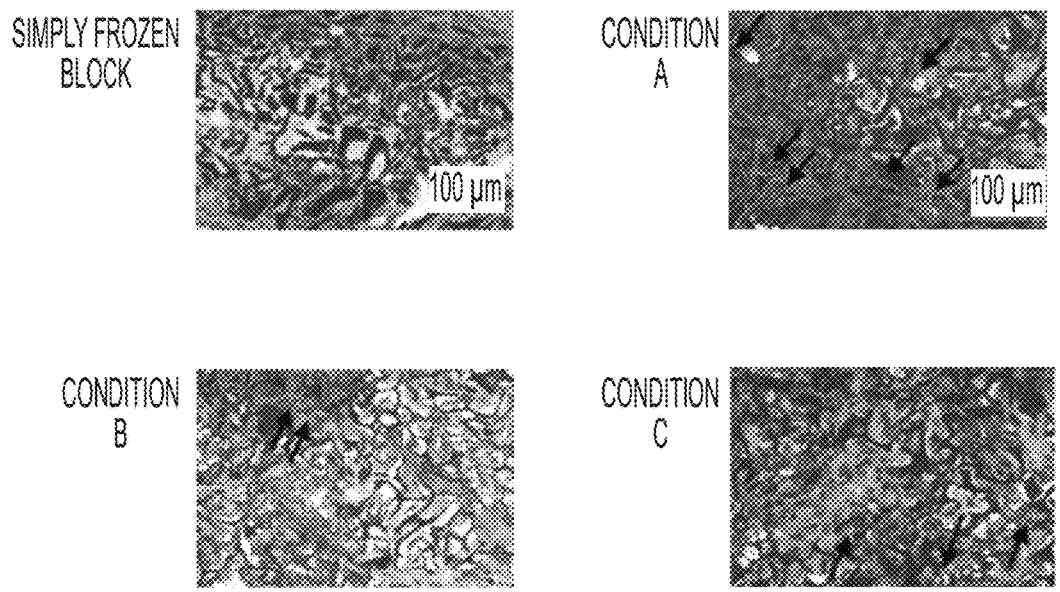
FIG. 7 shows Hematoxylin-Eosin (HE) samples produced two weeks after transplantation of hMSC mosaic cell aggregations in Example 8 (conditions A, B, and C) or in Comparative Example 6 (simply frozen block), under the skin.

In Example 12, HE samples obtained two weeks after transplantation of hMSC mosaic cell aggregations in Example 8 or in Comparative Example 6, under the skin are shown in FIG. 7. The number of cells described in FIG. 7 is the number of all live cells in the image, and the number of blood vessels is a value which is obtained by converting the number of blood vessels in each image per the area.

It can be seen that many blood vessels are formed and there are many cells survived, in the mosaic cell aggregations in which the blocks under the condition A, B, or C (condition A: the number of live cells being 244 cells, 61 blood vessels/mm$^3$, condition B: the number of live cells being 98 cells, 20 blood vessels/mm$^3$, and condition C: the number of live cells being 168 cells, 31 blood vessels/mm$^3$) in Example 8 are used, compared to the mosaic cell aggregations in which the simply frozen blocks in Comparative Example 6 (number of live cells being 81 cells, 0 blood vessel/mm$^3$) are used.

As described above, it can be seen that blood vessels are formed in the mosaic cell aggregation in which blocks of "condition A" at a proportion of 28% of cells, 57% of voids, and 15% of biocompatible macromolecular blocks in Example 8 are used, the mosaic cell aggregation in which blocks of "condition B" at a proportion of 41% of cells, 35% of voids, and 24% of biocompatible macromolecular blocks in Example 8 are used, and the mosaic cell aggregation in which blocks of the "condition C" at a proportion of 42% of cells, 44% of voids, and 14% of blocks in Example 8 are used whereas no blood vessel is formed in the mosaic cell aggregation in which simply frozen blocks at a proportion of 28% of cells, 32% of voids, and 40% of biocompatible macromolecular blocks in Comparative Example 6 are used. From the results of the above, it can be seen that it is possible to achieve angiogenesis in a case where a mosaic cell aggregation of which the volume proportion satisfies 20% to 50% of cells, 35% to 60% of voids, and 10% to 30% of biocompatible macromolecular blocks is used.

In addition, evaluation of samples was performed on the mosaic cell aggregations (of which the size of a CBE3 block was 53 to 106 μm) in which simply frozen blocks in Comparative Example 6 were used, and the mosaic cell aggregations in which a block (of which the size of a CBE3 block was 53 to 106 μm) under the condition B in Example 8 was used, in accordance with the following criteria. Each evaluation item was evaluated in stages using a four-point system.

Angiogenesis:

Angiogenesis was evaluated in four stages as follows. The angiogenesis was evaluated as 0 points in a case where there was no blood vessel, 1 point in a case where blood vessels existed in a low density, 2 points in a case where blood vessels existed in an approximately medium density, and 3 points in a case where blood vessels existed in a high density.

Cell Survival:

Cell survival was evaluated in four stages as follows. The cell survival was evaluated as 0 points in a case where there was almost no live cell, 1 point in a case where live cells existed sparsely, 2 points in a case where live cells were crowded, and 3 points in a case where live cells existed such that the proportion was fully occupied by live cells.

Cell Death:

Dead cells were evaluated in four stages as follows. The dead cells were evaluated as 0 points in a case where there was no dead cell, 1 point in a case where there was almost no dead cell, 2 points in a case where dead cells existed sparsely, and 3 points in a case where there were many dead cells.

The above-described results are shown in Table 2. Even from the results described in Table 2, it can be seen that angiogenesis is favorably performed in the mosaic cell aggregation in which the block in Example 8 is used compared to that in the mosaic cell aggregation in which the simply frozen block in Comparative Example 6 is used.

[Table 2]

TABLE 2

|  | Comparative Example 6 (simply frozen) | | Condition B in Example 8 (Present Invention) | |
| --- | --- | --- | --- | --- |
|  | After one week | After two weeks | After one week | After two weeks |
| Angiogenesis | 0.0 | 0.0 | 0.0 | 1.0 |
| Cell survival | 1.0 | 0.5 | 1.7 | 2.7 |
| Cell death | 1.0 | 0.0 | 0.3 | 0.0 |

Figure 8:
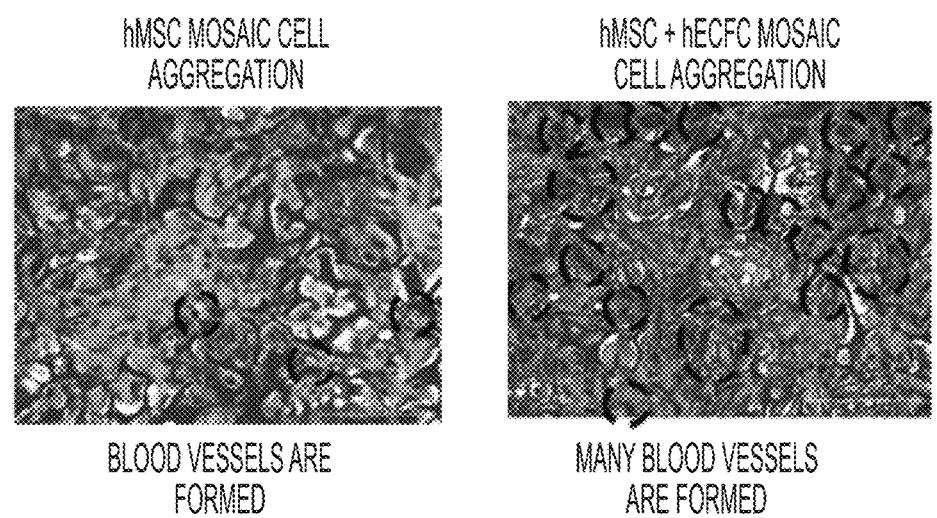
FIG. 8 shows HE samples produced two weeks after transplantation of an hMSC mosaic cell aggregation in which a block of the condition C in Example 8 is used or an hMSC+hECFC mosaic cell aggregation in which a block of the condition C in Example 9 is used, under the skin.

A result which is obtained by transplanting the hMSC+hECFC mosaic cell aggregation in the case where the block under the condition C in Example 9 is used, under the skin in Example 12, and a result which is obtained by transplanting the hMSC mosaic cell aggregation in a case where the block under the condition C in Example 8 is used, under the skin in Example 12 are shown in FIG. 8. When comparing the two results shown in FIG. 8 with each other, it can be seen that many blood vessels are formed due to hECFC in the hMSC+hECFC mosaic cell aggregation in Example 9.

Figure 9:
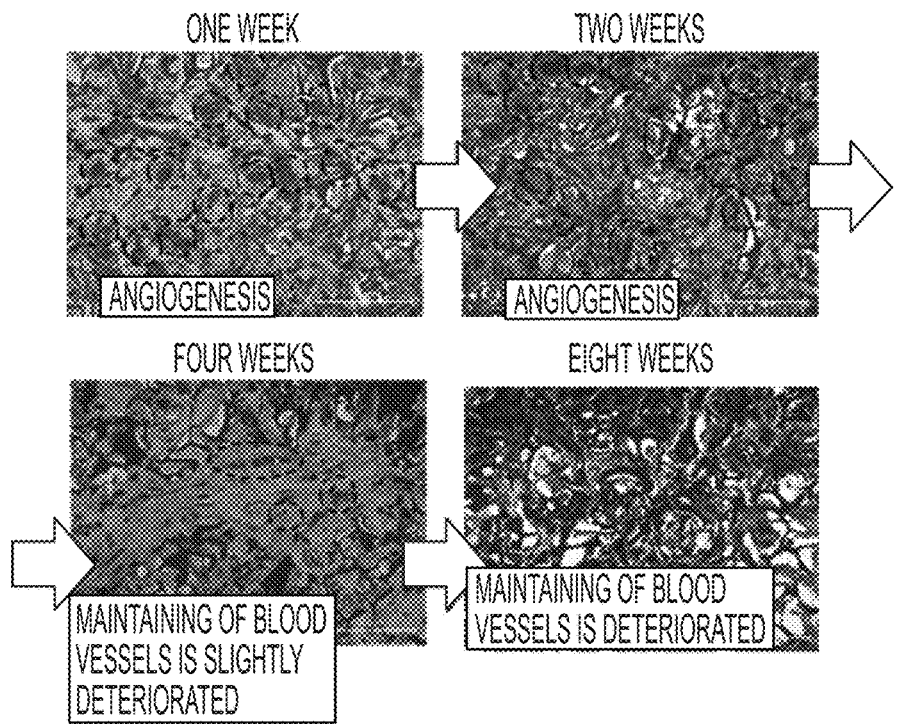
FIG. 9 shows a temporal change of an HE sample when transplanting the hMSC+hECFC mosaic cell aggregation in a case where the block of the condition C in Example 9 is used, under the skin.

In addition, the temporal change when transplanting the hMSC+hECFC mosaic cell aggregation in the case where the block (of which the size of a CBE3 block is 53 to 106 μm) under the condition C in Example 9 is used, under the skin in Example 12 is shown in FIG. 9. It can be seen that although many blood vessels are formed one week and two weeks after the transplantation due to hECFC, it is slightly difficult to maintain the formed blood vessels four weeks and eight weeks after the transplantation.

Figure 10:
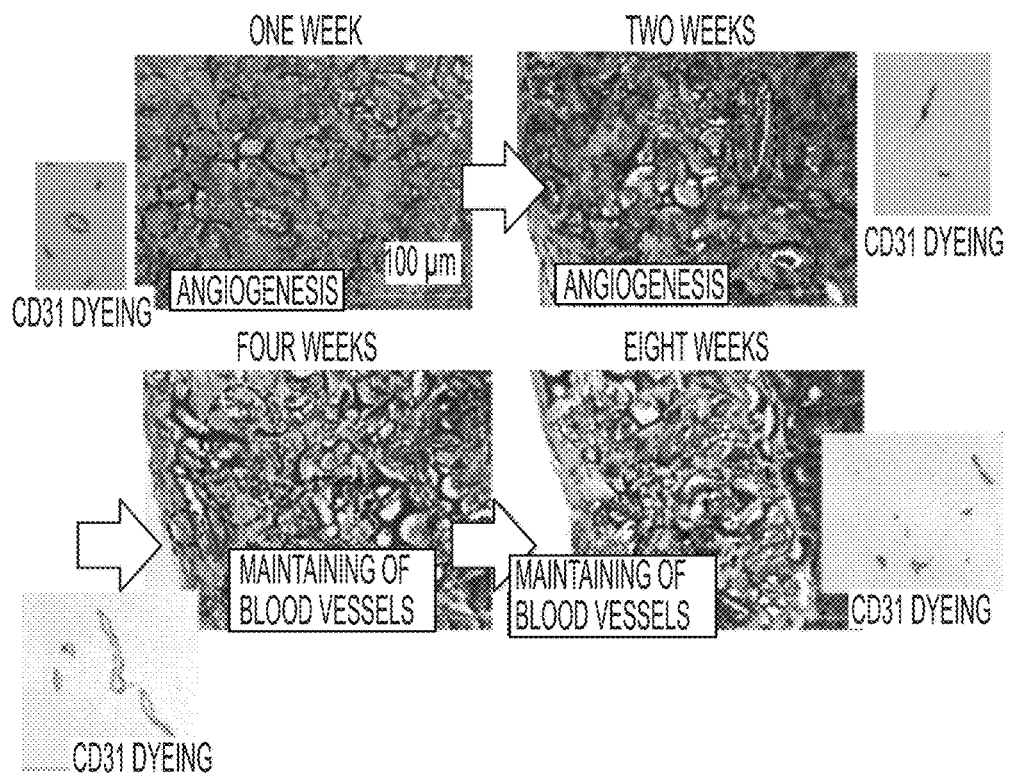
FIG. 10 shows a temporal change of an HE sample when transplanting the hMSC+hECFC mosaic cell aggregation in Example 9 under the renal capsule.

In contrast, a result which is obtained by transplanting the hMSC+hECFC mosaic cell aggregation in Example 9 under the renal capsule in Example 13 is shown in FIG. 10. It was found that blood vessels which had been formed exist four weeks after the transplantation under the renal capsule unlike the transplantation under the skin and the existence was further maintained up until eight weeks after the transplantation. It was shown that there were blood vessels derived from hECFC even four weeks and eight weeks after the transplantation if immunological dyeing was performed using a CD31 antibody for hECFC dyeing.

Figure 11:
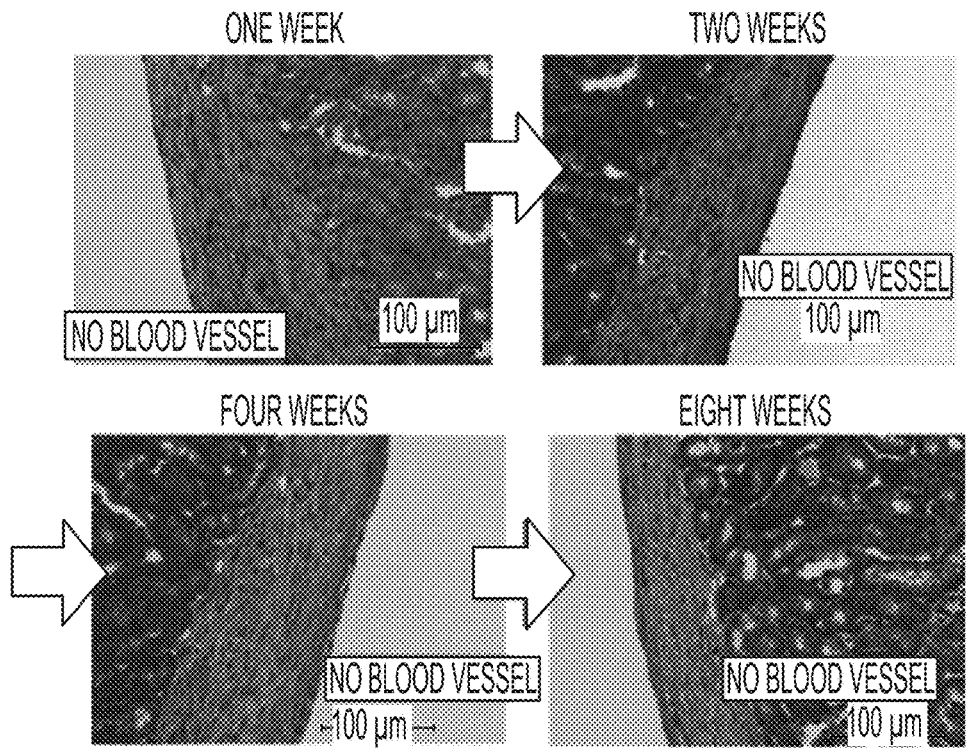
FIG. 11 shows a temporal change of an HE sample when transplanting an hMSC+hECFC cell aggregation in Comparative Example 7 under the renal capsule.

Since blood vessels were not formed in a case where the cell aggregation in Comparative Example 7 was transplanted under the renal capsule, there was no blood vessel found up until eight weeks after the transplantation (FIG. 11). It was shown that it was possible to form blood vessels and also to maintain blood vessels for a long period of time, due to the provision of a mosaic cell aggregation of the present invention under the renal capsule. Analysis of angiogenesis, cell survival, and cell death was performed on the obtained sample similarly to Example 15. In addition, evaluation of plasma accumulation and fibrillization was performed as follows.

Plasma Accumulation:

Plasma accumulation was evaluated in four stages as follows. The plasma accumulation was evaluated as 0 points in a case where there was no plasma, 1 point in a case where plasma existed slightly, 2 points in a case where there was a large amount of plasma, and 3 points in a case where a sample was filled with plasma.

Fibrillization:

Fibrillization was evaluated in four stages as follows. The fibrillization was evaluated as 0 points in a case where a sample was not fibrillized, 1 point in a case where fiber was slightly formed, 2 points in a case where fibrillization was in progress, and 3 points in a case where fibrillization had progressed and fiber is completely formed.

The above-described evaluation results are shown in Table 3. Even from the results in Table 3, it can be seen that blood vessels are maintained for a long period of time by placing a cell aggregation under the renal capsule rather than under the skin.

TABLE 3

|  | hECFC + hMSC mosaic cell aggregation/under skin | | | | hECFC + hMSC mosaic cell aggregation/under renal capsule | | | | hECFC + hMSC cell aggregation/under renal capsule | | | |
| --- | --- | --- | --- | --- | --- | --- | --- | --- | --- | --- | --- | --- |
|  | One week | Two weeks | Four weeks | Eight weeks | One week | Two weeks | Four weeks | Eight weeks | One week | Two weeks | Four weeks | Eight weeks |
| Angiogenesis | 2.0 | 1.7 | 0.7 | 0.3 | 2.7 | 1.7 | 1.3 | 2.0 | 0.0 | 0.0 | 0.3 | 0.3 |
| Cell survival | 2.7 | 2.3 | 1.7 | 0.3 | 3.0 | 3.0 | 2.7 | 2.5 | 2.0 | 1.0 | 0.0 | 0.0 |
| Cell death | 0.7 | 0.0 | 0.0 | 0.0 | 0.3 | 0.7 | 0.0 | 0.0 | 1.0 | 1.5 | 1.7 | 0.0 |
| Plasma accumulation | 1.3 | 1.3 | 0.7 | 0.0 | 3.0 | 2.3 | 2.3 | 1.0 | 0.0 | 0.5 | 0.7 | 0.0 |
| Fibrillization | 0.0 | 0.0 | 1.0 | 2.7 | 0.0 | 0.0 | 0.0 | 1.0 | 0.0 | 0.0 | 1.3 | 2.0 |

[Reference Example 1] Production of Recombinant Peptide Porous Body Condition D

The aluminum glass•cylindrical container was used, the final concentration of the aqueous CBE3 solution was 7.5 mass %, and the amount of aqueous solution was 4 mL. An aqueous CBE3 solution-contained aluminum glass•container was placed in a place of which the temperature of a shelf was set to be previously cooled down to −40° C., and freezing was performed while maintaining the temperature of the shelf at −40° C. as it was. Thereafter, freeze-drying was performed on the obtained frozen product to obtain a porous body.

[Reference Example 2] Production of Recombinant Peptide Block (Grinding and Cross-Linking of Porous Body)

The CBE3 porous body which had been produced under the condition D in Reference Example 1 was ground using new PowerMILL (Osaka Chemical Co., Ltd., new PowerMILL PM-2005). The grinding was performed for one minute×5 times, that is, for 5 minutes in total at the maximum rotation speed. The size of the obtained ground substance was divided using a stainless steel sieve to obtain CBE3 blocks of 25 to 53 µm, 53 to 106 µm, and 106 µm to 180 µm. Thereafter, recombinant peptide blocks were obtained by performing thermal cross-linking (performed for 8 to 48 hours of the cross-linking time) at 160° C. under reduced pressure.

[Example 16] Scanning Electron Microscope (SEM) Image and HE Sample of Biocompatible Macromolecular Block of Present Invention and Comparative Example Capturing of SEM images and Production of HE samples were performed in order to check the structures and the shapes of the surfaces of blocks with respect to the block (of which the size of a CBE3 block was 53 to 106 µm) under the condition A in Example 4, the block (of which the size of a CBE3 block was 53 to 106 µm) under the condition D in Reference Example 1, and the simply frozen block (of which the size of a CBE3 block was 53 to 106 µm) in Comparative Example 2. The SEM images are shown in FIG. 12 and the HE samples are shown in FIG. 13.

Figure 12:
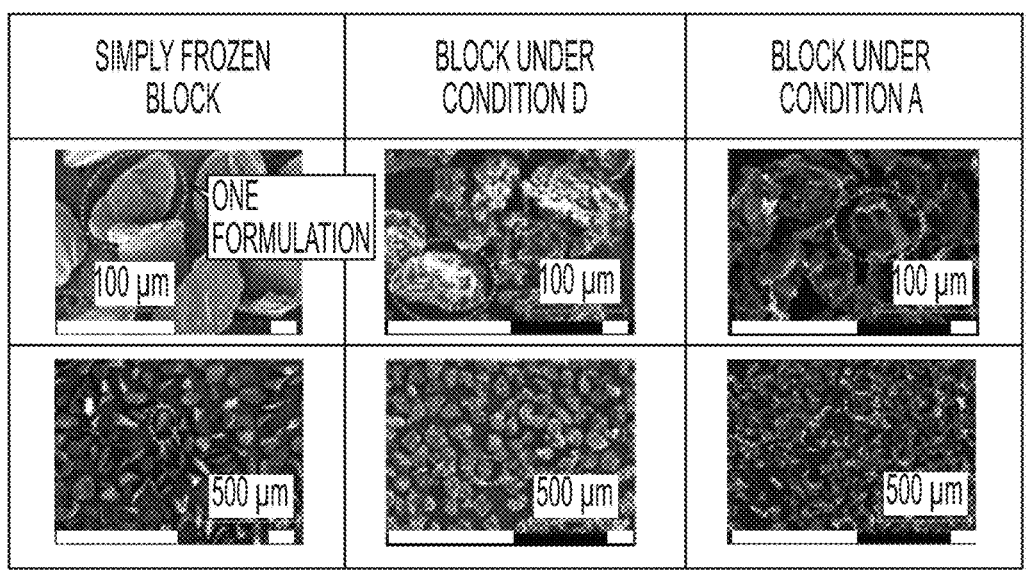
FIG. 12 shows scanning electron microscope (SEM) images of blocks of the condition A and a condition D in Example 4 and a simply frozen block in Comparative Example 2. Scales in the upper images show 100 µm and the scales in the lower images show 500 µm.
Figure 13:
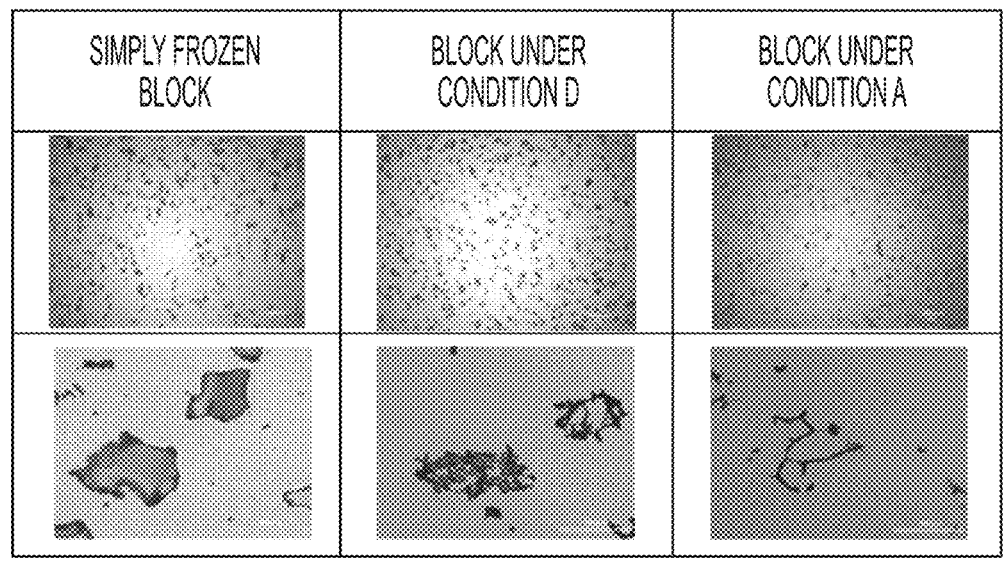
FIG. 13 shows HE piece images of blocks of the condition A and the condition D in Example 4 and the simply frozen block in Comparative Example 2. Scales show 100 µm.

It can be seen from the SEM images in FIG. 12 that either of the blocks in Example 4 and Reference Example 1 have roughness on the surfaces thereof and the structures thereof are complicated, whereas the surface of the simply frozen block in Comparative Example 2 is comparatively flat. This can also be checked by looking the HE samples in FIG. 13.

It is considered from the difference in the structures of these surfaces that the voids become large in the cell structure in which the blocks in Example 4 and Reference Example 1 are used, and the voids become small in the cell structure in which the block in Comparative Example 2 is used.

[Example 17] Scanning Electron Microscope (SEM) Image of Mosaic Cell Aggregation of Present Invention Human bone marrow-derived mesenchymal stem cells (hMSC) were adjusted to be $5 \times 10^3$ cells/mL using a proliferation medium (TAKARA BIO INC.: MSCGM BulletKit (registered trademark)), and CBE3 blocks (Condition A; the size of a CBE3 block was 53 to 106 µm) which had been produced in Example 4 were added thereto so as to make a concentration of 0.1 mg/mL. Then, 200 µL of the obtained mixture was sown in a Sumilon Celltight X96U plate (of which the bottom was in a U-shape, Sumitomo Bakelite Co., Ltd.), and the plate was centrifuged in Mini Plate Centrifuge (600 g, 5 minutes) and was allowed to stand for 24 hours. Capturing of SEM images was performed on the produced mosaic cell aggregation. The SEM images are shown in FIG. 14.

Figure 14:
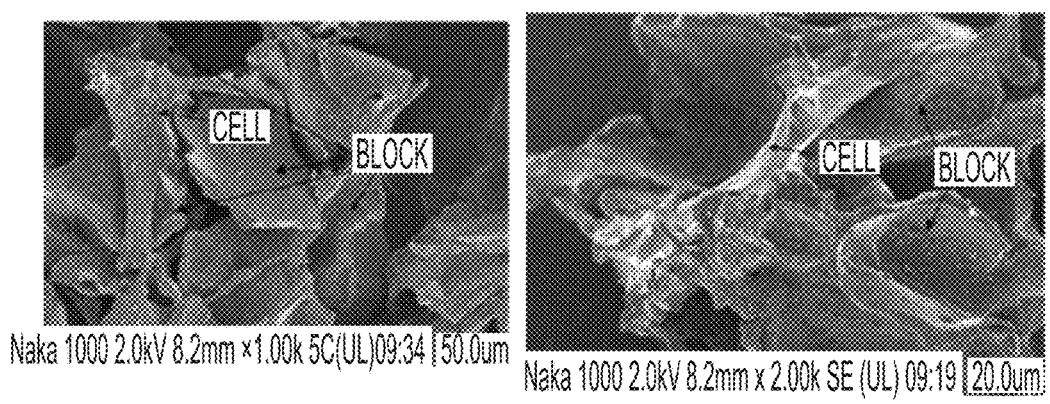
FIG. 14 shows scanning electron microscope (SEM) images of a mosaic cell aggregation in which a block of the condition A in Example 4 is used.

The status in which cells join a plurality of blocks together can be seen from the SEM images in FIG. 14. Furthermore, hMSC was adhered to the blocks by joining convex portions without entering concave portions of the blocks.

Accordingly, gaps through which a culture solution or oxygen passes are formed. This suggests that cells exist even in the mosaic cell aggregation due to liquid-gas exchange through the gaps.

What is claimed is:

1. A cell structure which contains a biocompatible macromolecular block and at least one kind of cell and has voids and in which a plurality of the biocompatible macromolecular blocks are arranged in gaps between a plurality of the cells,
wherein a ratio of the volume of the biocompatible macromolecular blocks with respect to the volume of the cell structure is 10% to 30%, a ratio of the volume of the cells with respect to the volume of the cell structure is 20% to 50%, and a ratio of the volume of the voids with respect to the volume of the cell structure is 35% to 60%;
wherein the biocompatible macromolecular block is a recombinant peptide.

2. The cell structure according to claim 1,
wherein the cells include at least human mesenchymal stem cells.

3. The cell structure according to claim 1,
wherein the cells include at least vascular cells.

4. The cell structure according to claim 1,
wherein the size of one of the biocompatible macromolecular blocks is 10 μm to 300 μm.

5. The cell structure according to claim 1,
wherein the thickness or the diameter of the cell structure is 400 μm to 3 cm.

6. The cell structure according to claim 1,
wherein the biocompatible macromolecular block consists of a recombinant peptide.

7. The cell structure according to claim 6,
wherein the recombinant peptide is any of
a peptide formed of an amino acid sequence described in SEQ ID No: 1,
a peptide which consists of an amino acid sequence in which one or a plurality of amino acids are deleted, substituted, or added in the amino acid sequence described in SEQ ID No: 1, and has biocompatibility, or
a peptide which consists of an amino acid sequence having 80% or more sequence identity to the amino acid sequence described in SEQ ID No: 1, and has biocompatibility.

8. The cell structure according to claim 1,
wherein, in the biocompatible macromolecular block, the biocompatible macromolecules are cross-linked using heat, ultraviolet rays, or enzymes.

9. The cell structure according to claim 1,
wherein the biocompatible macromolecular block is a biocompatible macromolecular block produced through a method including
a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and
a step (b) of freeze-drying the frozen biocompatible macromolecules which have been obtained in the step (a).

10. The cell structure according to claim 1,
wherein the biocompatible macromolecular block is a biocompatible macromolecular block produced through a method including
the step (a) of freezing the solution of the biocompatible macromolecules through the freezing treatment in which the highest internal liquid temperature, which is a liquid temperature in a portion having the highest liquid temperature within the solution, becomes lower than or equal to a temperature which is 3° C. lower than a melting point of a solvent in an unfrozen state,
the step (b) of freeze-drying the frozen biocompatible macromolecules which have been obtained in the step (a), and
a step (c) of grinding a porous body which has been obtained in the step (b).

11. The cell structure according to claim 1,
wherein blood vessels are formed inside the cell structure.

12. A cell structure obtained by merging a plurality of the cell structures according to claim 1, with each other.

13. The cell structure according to claim 1, wherein the recombinant peptide is a recombinant gelatin.

14. The cell structure according to claim 13, wherein the recombinant gelatin is cross-linked using heat.

15. A method for producing the cell structure according to claim 1, the method comprising:
a step of mixing at least one kind of cell with the biocompatible macromolecular block produced through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature which is 3° C. lower than a melting point of a solvent in an unfrozen state, and a step (b) of freeze-drying the frozen biocompatible macromolecules which have been obtained in the step (a).

16. A method for cell transplantation which comprises transplanting the cell structure of claim 1 into the renal capsule of a patient in need thereof.

17. The method according to claim 16, wherein the cell includes mesenchymal stem cells.

* * * * *